United States Patent
Nitta et al.

(10) Patent No.: US 10,214,429 B2
(45) Date of Patent: Feb. 26, 2019

(54) PHOSPHOR CONTAINING CE

(71) Applicant: Panasonic Intellectual Property Management Co., Ltd., Osaka (JP)

(72) Inventors: Mitsuru Nitta, Kyoto (JP); Yasuhisa Inada, Osaka (JP); Nobuaki Nagao, Gifu (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 49 days.

(21) Appl. No.: 15/636,747

(22) Filed: Jun. 29, 2017

(65) Prior Publication Data

US 2018/0002188 A1 Jan. 4, 2018

Related U.S. Application Data

(63) Continuation of application No. PCT/JP2017/000935, filed on Jan. 13, 2017.

(30) Foreign Application Priority Data

Jul. 4, 2016 (JP) .................. 2016-132126

(51) Int. Cl.

| | |
|---|---|
| *C01F 17/00* | (2006.01) |
| *G01N 23/20* | (2018.01) |
| *C09K 11/77* | (2006.01) |
| *F21S 41/20* | (2018.01) |
| *F21S 41/32* | (2018.01) |
| *F21S 41/16* | (2018.01) |
| *F21S 41/176* | (2018.01) |
| *G01N 21/64* | (2006.01) |
| *H01S 5/00* | (2006.01) |

(52) U.S. Cl.
CPC ...... *C01F 17/0012* (2013.01); *C09K 11/7774* (2013.01); *F21S 41/16* (2018.01); *F21S 41/176* (2018.01); *F21S 41/285* (2018.01); *F21S 41/321* (2018.01); *G01N 23/20* (2013.01); *C01P 2002/22* (2013.01); *C01P 2002/70* (2013.01); *C01P 2002/72* (2013.01); *C01P 2002/76* (2013.01); *C01P 2002/84* (2013.01); *G01N 2021/6417* (2013.01); *H01S 5/005* (2013.01)

(58) Field of Classification Search
CPC ..... C01F 17/00; C01F 17/0012; F21S 41/176; F21S 41/16; G01N 23/20

USPC .................................................. 252/301.4 F
See application file for complete search history.

(56) References Cited

U.S. PATENT DOCUMENTS

| | | | | |
|---|---|---|---|---|
| 9,725,648 | B2* | 8/2017 | Izawa | ................ C09K 11/0883 |
| 2005/0242329 | A1 | 11/2005 | Fiedler et al. | |
| 2006/0197098 | A1 | 9/2006 | Aihara | |

FOREIGN PATENT DOCUMENTS

| | | |
|---|---|---|
| JP | 2006-008721 | 1/2006 |
| JP | 2006-245443 A | 9/2006 |
| JP | 2007-515527 A | 6/2007 |
| JP | 2008-088362 | 4/2008 |
| JP | 2009-512741 A | 3/2009 |
| JP | 2009-249445 | 10/2009 |
| JP | 2011-526066 A | 9/2011 |
| JP | 2014-224230 | 12/2014 |
| JP | 2016-028124 | 2/2016 |
| WO | 2007/041563 A2 | 4/2007 |
| WO | 2009/157999 A1 | 12/2009 |
| WO | 2015/025570 | 2/2015 |

OTHER PUBLICATIONS

R. Le Toquin et al., "Red-emitting cerium-based phosphor materials for solid-state lighting applications", Chemical Physics Letters, vol. 23, Issues4-6, Jun. 1, 2006, pp. 352-356.
"Qiang-Qiang Zhu et al., ""Extra-Broad Band Orange-Emitting Ce3+-Doped Y3Si5N9O Phosphor for Solid-State Lighting: Electronic, Crystal Structures and Luminescence Properties""", Chemistry of Materials, vol. 28, Jun. 20, 2016, pp. 4829-4839."
International Search Report of PCT application No. PCT/JP2017/000935 dated Mar. 7, 2017.

* cited by examiner

*Primary Examiner* — Edward M Johnson
(74) *Attorney, Agent, or Firm* — McDermott Will & Emery LLP

(57) ABSTRACT

A phosphor contains a crystal phase having a chemical composition $Ce_xM_{3-x-y}\beta_6\gamma_{11-z}$. M is one or more elements selected from the group consisting of Sc, Y, La, Pr, Nd, Sm, Eu, Gd, Tb, Dy, Ho, Er, Tm, Yb, and Lu. $\beta$ contains Si in an amount of 50 mol % or more of a total mol of $\beta$. $\gamma$ contains N in an amount of 80 mol % or more N of a total mol of $\gamma$. x satisfies $0<x\leq0.6$. y satisfies $0\leq y\leq1.0$. z satisfies $0\leq z\leq1.0$. The phosphor shows a maximum peak of an emission spectrum in a wavelength range of 600 nm or more and 800 nm or less and a first peak of an excitation spectrum in a wavelength range of 500 nm or more and 600 nm or less.

22 Claims, 18 Drawing Sheets

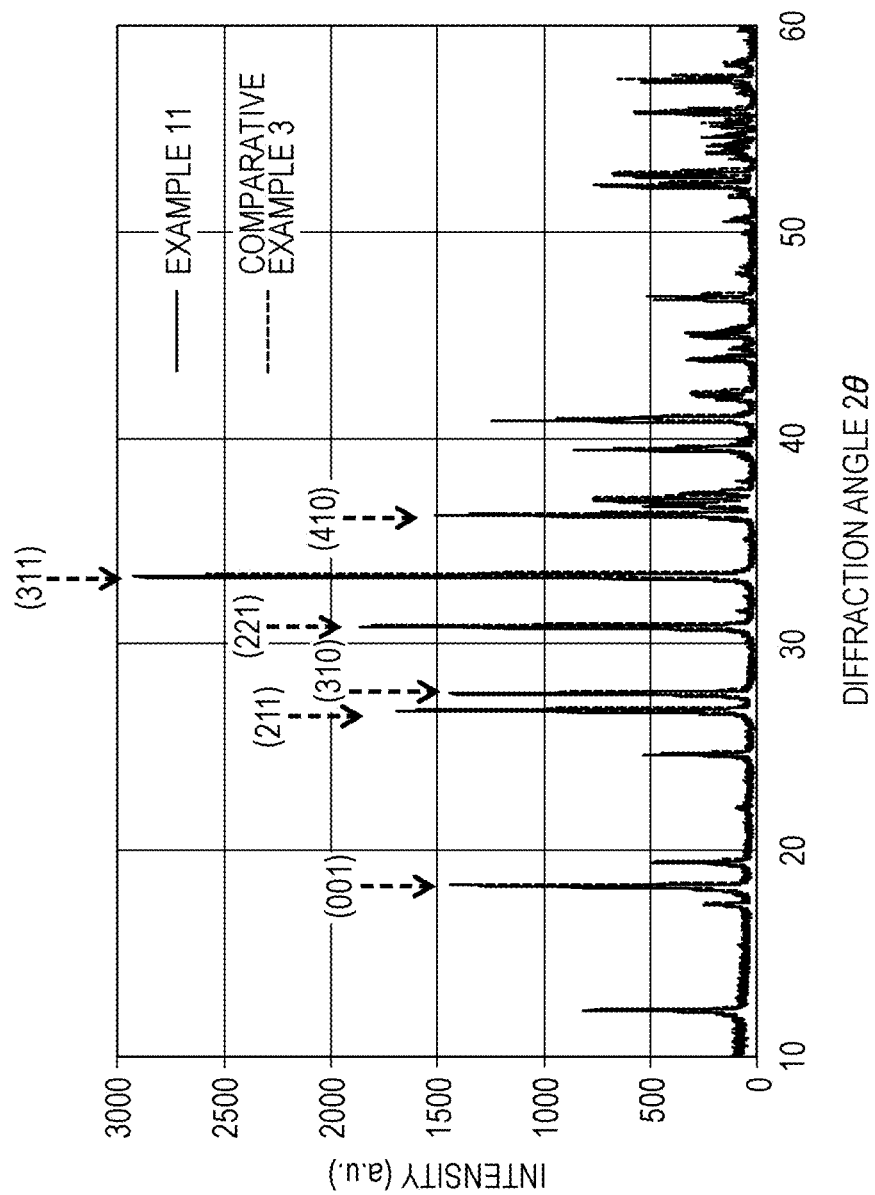

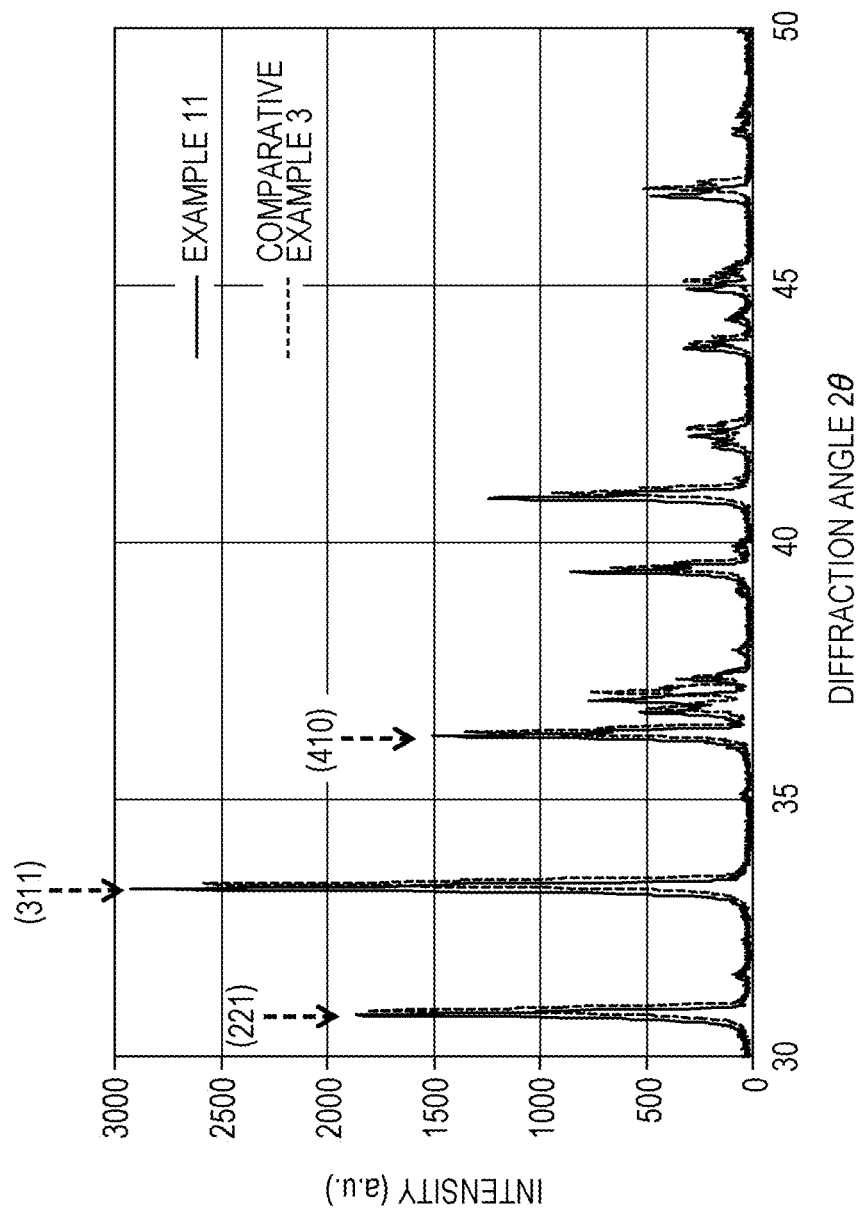

PHOSPHOR CONTAINING CE

BACKGROUND

1. Technical Field

The present disclosure relates to a phosphor and a light-emitting apparatus.

2. Description of the Related Art

In recent years, solid state light sources, such as white light emitting diodes (LEDs) and laser excitation light sources, have been widely used. A current general white LED has a structure of a combination of a blue light emitting element (blue LED chip) and a phosphor. In such a general white LED, white light is generated by converting the color of a part of light from the blue LED chip with the phosphor and mixing the blue light from the blue LED chip and the light from the phosphor. More recently, a high-output white light-emitting apparatus by a combination of a laser diode (LD) and a phosphor is also being developed. As the solid state white-light source, a combination of a blue LED chip or blue LD and a yellow phosphor is currently predominate, but a white light source of a combination of a blue light source, a yellow phosphor, and also a red phosphor is being developed for the purpose of enhancing, for example, color rendering properties and color reproducibility or for obtaining white with low color temperature.

Yellow phosphors having Ce as the emission centers represented by, for example, the formula $Y_3Al_5O_{12}:Ce^{3+}$ (hereinafter, abbreviated as YAG:Ce) or the formula $La_3Si_6N_{11}:Ce^{3+}$ (hereinafter, abbreviated as LSN:Ce) described in Japanese Patent No. 4459941 have been known. In addition, red phosphors having Eu as the emission centers represented by, for example, the formula $(Sr,Ca)AlSiN_3:Eu^{2+}$ (hereinafter, abbreviated as CASN:Eu) described in Japanese Patent No. 3837588 have been known.

SUMMARY

One non-limiting and exemplary embodiment provides a phosphor having Ce as the emission center.

In one general aspect, the techniques disclosed here feature a phosphor containing a crystal phase having a chemical composition $Ce_xM_{3-x-y}\beta_6\gamma_{11-z}$, where M is one or more elements selected from the group consisting of Sc, Y, La, Pr, Nd, Sm, Eu, Gd, Tb, Dy, Ho, Er, Tm, Yb, and Lu; $\beta$ contains Si in an amount of 50 mol % or more of a total mol of $\beta$; $\gamma$ contains N in an amount of 80 mol % or more of a total mol of $\gamma$; and $0<x\leq0.6$, $0\leq y\leq1.0$, and $0\leq z\leq1.0$. An emission spectrum of the phosphor has a maximum peak in a wavelength range of 600 nm or more and 800 nm or less. An excitation spectrum of the phosphor has a first peak in a wavelength range of 500 nm or more and 600 nm or less.

The generic or specific aspect of the present disclosure may be realized as a phosphor, an element, an apparatus, a system, a vehicle, a manufacturing method, or any combination thereof.

The phosphor of the present disclosure contains Ce as the emission center.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 21A shows XRD diffraction patterns of Example 11 and Comparative Example 3;

FIG. 21B is an enlarged graph of the XRD diffraction patterns of Example 11 and Comparative Example 3;

DETAILED DESCRIPTION

Figure 1:
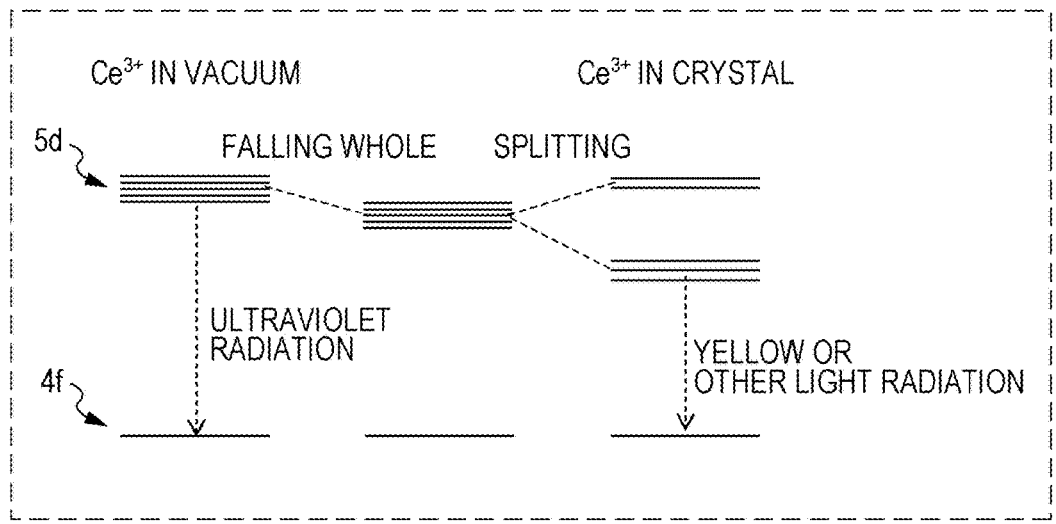
FIG. 1 is an energy level diagram of $Ce^{3+}$ in vacuum and in the crystal.

Knowledge Forming the Basis of the Present Disclosure

A yellow phosphor YAG:Ce has high emission quantum efficiency and does hardly change the emission quantum efficiency even if it is excited with a high-output LED or LD and is therefore mounted on almost all white light sources. In contrast, a red phosphor CASN:Eu has a problem of decreasing the emission quantum efficiency when excited with high-output light and is mounted on only light sources of relatively low outputs. This is because a phosphor containing Eu as the emission center has a relatively long emission lifetime, compared to a phosphor containing Ce as the emission center, and thus, the brightness is readily saturated under high-output excitation. Accordingly, the present inventors have diligently studied in order to obtain a red phosphor containing Ce as the emission center.

Embodiments of the present disclosure will now be described in detail. It should be understood that the present disclosure is not limited to these Embodiments and can be implemented with appropriate modifications within a scope not departing from the technical scope of the present disclosure.

Embodiment 1

The phosphor of Embodiment 1 contains a crystal phase having a chemical composition $Ce_xM_{3-x-y}\beta_6\gamma_{11-z}$, where x satisfies $0<x\leq0.6$. In order to obtain light emission, it is necessary to contain Ce. Accordingly, x is larger than 0 and is desirably 0.0003 or more and more desirably 0.015 or more from the viewpoint of increasing the emission intensity. As long as the phosphor can emit light, the maximum value of x is not particularly limited. However, if the value of x is excessively large, the emission intensity decreases by concentration quenching. Therefore, the decrease in emission intensity can be prevented by limiting x to 0.6 or less. In addition, x is desirably 0.3 or less and more desirably 0.15 or less from the viewpoint of increasing the emission intensity.

M represents a rare-earth element other than Ce and is specifically one or more elements selected from the group consisting of Sc, Y, La, Pr, Nd, Sm, Eu, Gd, Tb, Dy, Ho, Er, Tm, Yb, and Lu. In addition, M may contain La in an amount of 90 mol % or more of a total mol of M. The elements, other than La, belonging to the above-mentioned group have ion radii similar to that of La and therefore can enter the M-site.

y satisfies $0\leq y\leq1.0$. If y is larger than 1.0, the structure becomes unstable. Accordingly, the structure can be stabilized by limiting y to 1.0 or less.

β contains Si in an amount of 50 mol % or more of a total mol of β. That is, β is composed of Si only or composed of 50 mol % or more Si and 50 mol % or less other element or elements. In addition, β may contain, for example, one or two elements selected from the group consisting of Al and Ga. Furthermore, (100x/6) mol % or more of may be such one or two elements. That is, in $Ce_xM_{3-x-y}\beta_6\gamma_{11-z}$, the molar number of such one or two elements may be larger than that of Ce. In addition, (300x/6) mol % or more of β may be such one or two elements. That is, in $Ce_xM_{3-x-y}\beta_6\gamma_{11-z}$, the molar number of such one or two elements may be three times or more that of Ce. In addition, β may further contain another element as long as the phosphor can emit light.

γ contains N in an amount 80 mol % or more of a total mol of γ. That is, γ is composed of N only or composed of 80 mol % or more N and 20 mol % or less other element or elements. In addition, γ may contain, for example, O (oxygen). Thus, for example, the symmetry of the ligands of Ce decreases by substituting a part of the Si-site in the vicinity of Ce with Al (or Ga) or by substituting a part of the N-site with O, and emission of light with a longer wavelength can be realized.

z satisfies $0\leq z\leq1.0$. If there is a deficit of N (i.e., when z is larger than O), the symmetry of the ligands of Ce decreases and emission of light with a longer wavelength can be realized. In addition, when z is larger than 1.0, the structure becomes unstable. Accordingly, the structure can be stabilized by limiting z to 1.0 or less.

The phosphor of Embodiment 1 has a maximum peak of an emission spectrum in a wavelength range of 600 nm or more and 800 nm or less. Herein, the maximum peak is a peak having a maximum value in the whole spectrum. The peak of the above-described emission spectrum appears, for example, by excitation at a wavelength of 535 nm.

In addition, the phosphor of Embodiment 1 has a first peak of an excitation spectrum in a wavelength range of 500 nm or more and 600 nm or less. In addition, the phosphor of Embodiment 1 may further have a second peak of the excitation spectrum in a wavelength range of 350 nm or more and less than 500 nm. The first or second peak may be the maximum peak of the excitation spectrum.

The phosphor of Embodiment 1 may have a 1/e emission lifetime of 100 ns or less. The emission lifetime affects the brightness saturation characteristics. Known phosphors containing Eu, such as a red phosphor CASN:Eu, have long emission lifetimes, compared to phosphors containing Ce. Therefore, the phosphors containing Eu decrease the quantum efficiency under high-output excitation, and thereby the brightness is readily saturated. Accordingly, the phosphor of Embodiment 1 containing Ce as the emission center is promising as a red phosphor having high quantum efficiency even under high output, compared to known red phosphors.

The crystal phase having a chemical composition $Ce_xM_{3-x-y}\beta_6\gamma_{11-z}$, in the phosphor of Embodiment 1 may be a tetragon. The crystal phase may contain a region having a space group P4bm (#100). The above-described crystal phase in Embodiment 1 may have almost the same crystal structure as that of the crystal represented by the formula $La_3Si_6N_{11}$.

The X-ray diffraction pattern using Cu-Kα radiation of the phosphor of Embodiment 1 may have diffraction peaks in (1) 2θ: 17.8° or more and 18.8° or less, (2) 2θ: 26.2° or more and 27.2° or less, (3) 2θ: 27.2° or more and 28.2° or less, (4) 2θ: 30.5° or more and 31.5° or less, (5) 2θ: 32.8° or more and 33.8° or less, and (6) 2θ: 35.8° or more and 36.8° or less. The plane indices indicated by these diffraction peaks may be (001), (211), (310), (221), (311), and (410), respectively.

The above-described crystal phase in Embodiment 1 may have the following characteristics in XAFS (X-ray absorption fine structure) measurement. In an EXAFS (extended X-ray absorption fine structure) radial distribution function spectrum at K-absorption edge of Ce, the height of the peak of the first neighbor shell of Ce may be lower than that of the peak of the second neighbor shell of Ce. The height of the peak of the first neighbor shell may be 0.8 times or more and 0.9 times or less the height of the peak of the second neighbor shell.

The coordination number of the first neighbor shell of Ce, which is obtained from the EXAFS radial distribution function spectrum at K-absorption edge of Ce, may be seven. In this case, the coordination structure in the vicinity of Ce may be, for example, a structure having nitrogen deficiency introduced in the vicinity of the A-site of La in $La_3Si_6N_{11}$, and may be a coordination structure of heptacoordination showing low symmetry. Known crystal represented by the formula $La_3Si_6N_{11}$ has a coordination structure of octacoordination showing high symmetry. Accordingly, in the coordination structure of heptacoordination showing low symmetry, the 5d orbit splitting becomes large, and the energy difference from the 4f orbit decreases. Consequently, emission of light with a wavelength longer than before can be realized.

The crystal phase described above may be a crystal phase represented by, for example, a chemical composition $Ce_xM_{3-x-y}Si_{6-q}A_qN_{11-z}$. On this occasion, M may be one or more elements selected from the group consisting of Sc, Y, La, Pr, Nd, Sm, Eu, Gd, Tb, Dy, Ho, Er, Tm, Yb, and Lu; A may be one or two elements selected from the group consisting of Al and Ga; x may satisfy $0<x\leq0.6$; y may satisfy $0\leq y\leq1.0$; z may satisfy $0\leq z\leq1.0$; and q may satisfy $x\leq q\leq3.0$.

Method of Producing Phosphor

A method of producing a phosphor of Embodiment 1 will now be described. As raw materials, for example, compounds containing Ce, La, Si, and Al (or Ga) may be used. Alternatively, each of Ce, La, Si, and Al (or Ga) may be used as a simple substance. As the compound, for example, a compound becoming a nitride by firing under a nitrogen atmosphere, a high-purity (purity: 99% or more) nitride, or a metal alloy can be used. In order to accelerate the reaction, a small amount of a fluoride (such as ammonium fluoride) may be added.

For example, a Ce compound, a La compound, and a Si compound (or Si simple substance) are prepared to give a chemical composition ratio represented by $Ce_xLa_{3-x-y}Si_6N_{11-z}$ ($0<x\leq0.6$, $0\leq y\leq1.0$, $0\leq z\leq1.0$), and an Al compound (or Al simple substance) may also be prepared. Specifically, as the raw materials, for example, a $CeF_3$ powder (or CeN powder), a LaN powder, a $Si_3N_4$ powder (or powder of Si simple substance), and an AlN powder (or powder of Al simple substance) may be used. The LaN powder may be prepared in an amount higher by about 24% than the theoretical value. Since LaN is readily decomposed during firing, generation of a by-product $LaSi_3N_5$ crystal can be suppressed by charging an excessive amount of LaN in blending of the raw materials.

The phosphor is produced by mixing the above-mentioned raw materials and firing them. The method of mixing the raw materials may be wet blending in a solution or dry blending of dry powders. A machine commonly used industrially, such as a ball mill, a medium stirring mill, a planetary mill, a vibration mill, a jet mill, a V-type mixer, or a stirrer, can be used. The firing is performed in an atmosphere pressurized with nitrogen within a temperature range of 1500° C. to 2000° C. for about 1 to 50 hours. The pressure in this case is usually 3 atm or more, desirably 4 atm or more, and more desirably 8 atm or more. The phosphor after firing may be washed, for example, in a 10% nitric acid solution for 1 hour. The resulting phosphor powder may be pulverized again with, for example, a ball mill or a jet mill and may be further washed or sorted as needed to adjust the particle size distribution and fluidity of the phosphor powder.

Crystal Structure Simulation of Phosphor

The results of studies with simulation by the present inventors on the crystal structure of the phosphor of Embodiment 1 will now be shown. $Ce^{3+}$ has one electron in the 4f orbit, which causes light emission by being excited to the 5d orbit. In addition, in a phosphor containing $Ce^{3+}$ as the emission center, the excited state of Ce is the 5d orbit, the ground state is the 4f orbit, and the excitation-emission transition is 4f-5d transition. $Ce^{3+}$ emits ultraviolet light in vacuum due to the large energy difference between the 4f and 5d orbits.

In contrast, as shown in FIG. 1, $Ce^{3+}$ entered in a crystal is affected by ligands and causes an effect of decreasing the whole energy of the 5d orbit and an effect of shifting the lowest level of the 5d orbit to the low energy side by removal of the degeneracy of the 5d orbit. Accordingly, the energy difference between the 4f and 5d orbits is decreased, and the emission wavelength becomes long. It is conceivable, according to the effects described above, for example, that in known YAG:Ce and LSN:Ce, the emission wavelength of $Ce^{3+}$ considerably shifts to the long wavelength side to emit yellow light.

Figure 2:
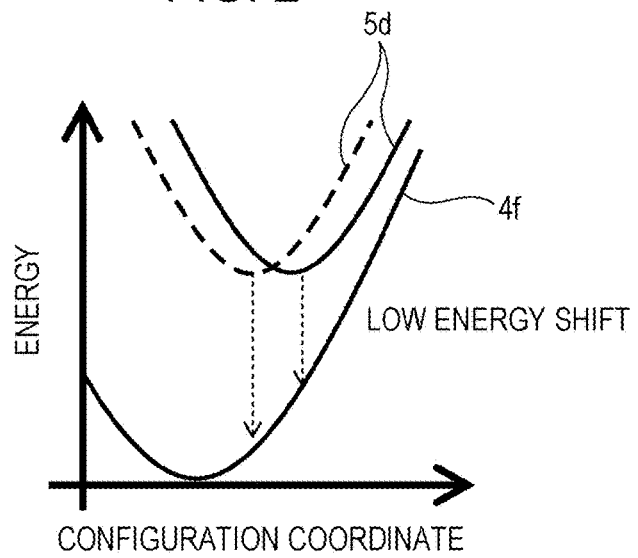
FIG. 2 is a model diagram of the configuration coordinate between the 4f orbit and the 5d orbit.

The crystal structure will be further considered based on the configuration coordinate model as shown in FIG. 2. If conditions for shifting the equilibrium points of the 4f orbit and the 5d orbit are achieved, the energy difference between the 4f and 5d orbits further decreases and the emission wavelength becomes long. That is, on this occasion, the symmetry of the ligands in the vicinity of Ce decreases according to the crystal ligand field theory, which removes the degeneracy of the 5d orbit to increase the orbit splitting width of the 5d orbit and decreases the energy level difference between the 4f and 5d orbits. Consequently, the emission wavelength becomes long.

Accordingly, the present inventors studied on crystals in which the ligands of Ce are asymmetry for elongating the emission wavelength of the phosphor. As a result, as described below, the inventors found a crystal structure that is believed to include ligands having symmetry further lower than that of the ligands of Ce in a known LSN:Ce yellow phosphor. The phosphor having a chemical composition LSN:Ce disclosed in Japanese Patent No. 4459941, which is an example of known LSN:Ce yellow phosphor, has a light emission peak wavelength of 574 to 594 nm and an excitation peak wavelength of 455 to 460 nm.

The results and consideration of crystal structure simulation are shown below. In order to investigate the site on which Ce can substitute in the crystal structure of $La_3Si_6N_{11}$, the La-site of $La_3Si_6N_{11}$ is substituted by Ce for structural optimization by first-principle calculation. In the first-principle calculation, CASTEP of Dassault Systemes Biovia K.K. was used. The functional used was GGA, and the exchange-correlation interaction used was PBE.

Figure 3:
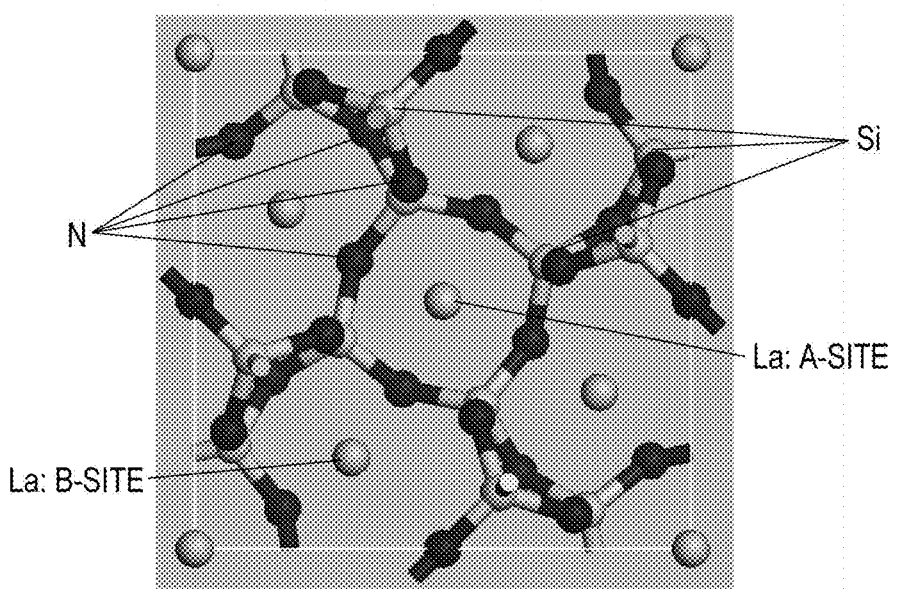
FIG. 3 is a diagram illustrating the 1×1×3 supercell structure of $La_3Si_6N_{11}$ subjected to structural optimization.
Figure 4:
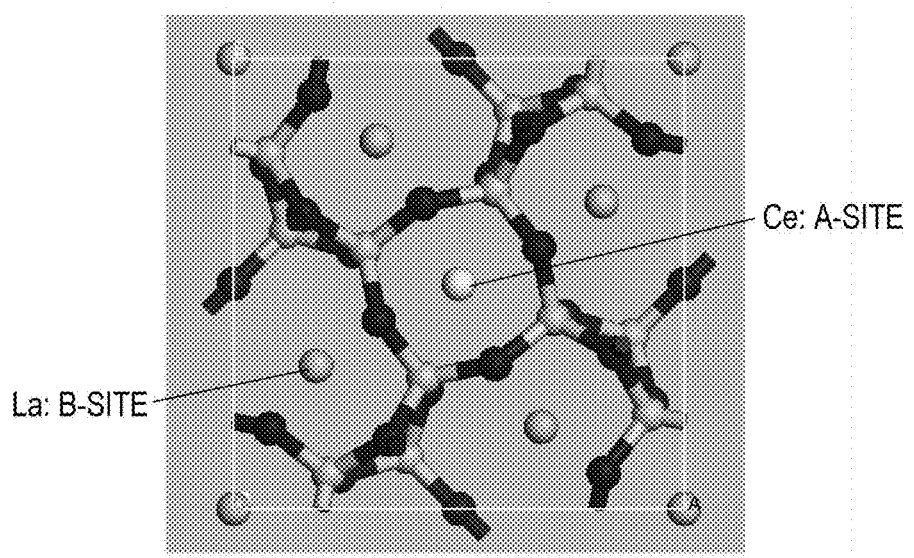
FIG. 4 is a diagram illustrating the 1×1×3 supercell structure of $La_3Si_6N_{11}:Ce$ substituted by Ce for La at the A-site and subjected to structural optimization.
Figure 5:
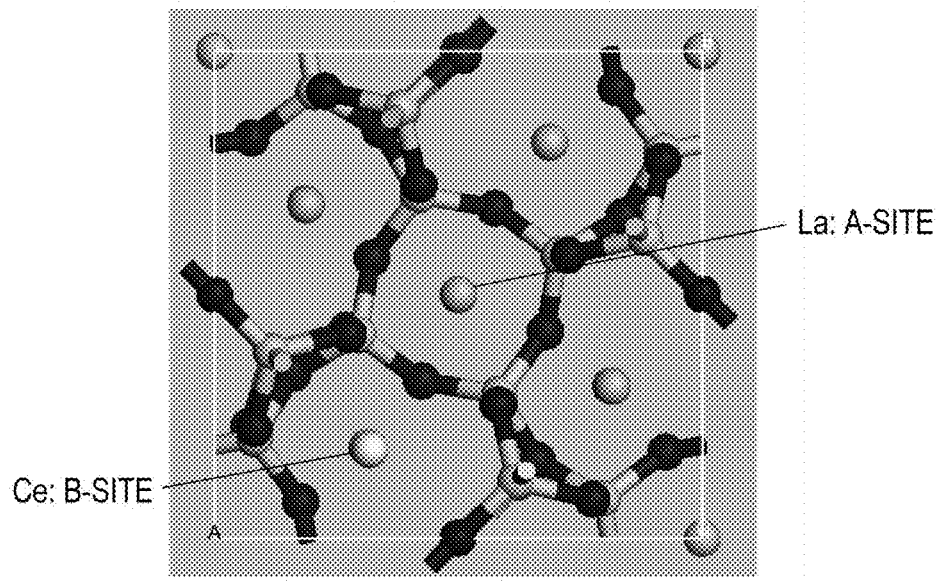
FIG. 5 is a diagram illustrating the 1×1×3 supercell structure of $La_3Si_6N_{11}:Ce$ substituted by Ce for La at the B-site and subjected to structural optimization.

FIG. 3 shows the result of structural optimization of the 1×1×3 supercell of $La_3Si_6N_{11}$. The space group of the unit cell of $La_3Si_6N_{11}$ is P4bm (#100), and the coordination state of La includes an A-site of high symmetry and a B-site of low symmetry. FIG. 4 shows crystal structure 1 substituted by Ce for La at the A-site and subjected to structural optimization. FIG. 5 shows crystal structure 2 substituted by Ce for La at the B-site and subjected to structural optimization.

As obvious from FIG. 4, eight N atoms are arranged almost equidistantly around Ce at the A-site. That is, in the structure, Ce is shared by two quadrangular pyramids as the apex, and the square bottoms are twisted from each other by 45° to give an 8 coordination structure having high symmetry of the ligands of Ce. In contrast, as obvious from FIG. 5, eight N atoms are arranged with different distances and different angles around Ce at the B-site, and the symmetry of the ligands of Ce is low compared to that at the A-site.

Table 1 shows the distances between Ce and N atoms and standard deviation thereof in crystal structure 1 substituted by Ce for La at the A-site of $La_3Si_6N_{11}$ crystal structure and crystal structure 2 substituted by Ce for La at the B-site of $La_3SiN_{11}$, in order to quantify the symmetry.

TABLE 1

|  | Ce—N distance (Å) | | | | | | | | Standard deviation σCe—N |
|---|---|---|---|---|---|---|---|---|---|
|  | Ce—N1 | Ce—N2 | Ce—N3 | Ce—N4 | Ce—N5 | Ce—N6 | Ce—N7 | Ce—N8 |  |
| Crystal structure 1 | 2.628 | 2.614 | 2.621 | 2.629 | 2.650 | 2.646 | 2.662 | 2.665 | 0.019 |
| Crystal structure 2 | 2.508 | 2.366 | 2.508 | 2.366 | 2.696 | 2.775 | 2.697 | 2.774 | 0.171 |
| Crystal structure 3 | 2.717 | 2.462 | 3.593 | 3.007 | 2.810 | 3.595 | 2.469 | 2.735 | 0.450 |
| Crystal structure 4 | 3.099 | 2.303 | 3.670 | 3.107 | 2.551 | 3.670 | 2.314 | 2.578 | 0.560 |

The results demonstrate that the symmetry of the Ce ligands of the crystal structure 2 substituted by Ce for La at the B-site is lower than that of the crystal structure 1 substituted by Ce for La at the A-site.

Furthermore, in order to investigate which of the A-site and the B-site of La is readily substituted by Ce, the enthalpy of formation of each crystal was calculated by first-principle calculation. As a result, it was revealed that crystal structure 1 substituted by Ce for La at the A-site has an enthalpy of formation lower by 48 meV than that of crystal structure 2 substituted by Ce for La at the B-site and is stable as a structure.

The above suggests a possibility that in known LSN:Ce yellow phosphors, for example, Ce is present at the A-site containing ligands with high symmetry and being energetically stable as in crystal structure 1, and thereby yellow light is emitted.

The above analytical results suggest a possibility that in $La_3Si_6N_{11}$:Ce substituted by Ce for La at the B-site such as crystal structure 2, the equilibrium points of the 4f and 5d orbits shift due to the low symmetry of the ligands of Ce, and emission of light with a longer wavelength compared to known LSN:Ce yellow phosphors can be realized.

Herein, since the red phosphor of Embodiment 1 may contain Al in the starting material, Al may be incorporated into the crystal phase of the phosphor. In addition, O contained in the raw material may be incorporated in the crystal phase of the phosphor. Si and Al have close ion radii and can be substituted by each other, and N and O can be similarly substituted by each other. Regarding the ion radius, Al>Si and N>O. Accordingly, the substitution for Si with Al increases the lattice constant, and the substitution for N with O decreases the lattice constant. That is, it is believed that the crystal can be more stabilized by simultaneously substituting Si and N with Al and O, respectively. In addition, the valence of the crystal can be maintained by simultaneously substituting Si and N with Al and O, respectively. Accordingly, the numbers of the moles of Al and O contained in the crystal phase may be the same.

Figure 6:
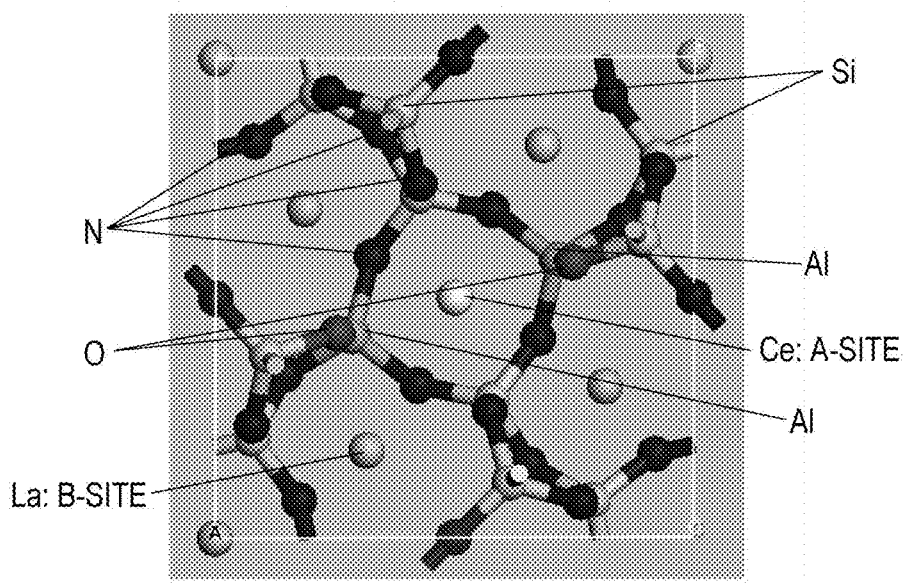
FIG. 6 is a diagram illustrating the 1×1×3 supercell structure of $La_3Si_6N_{11}:Ce$ substituted by Ce for La at the A-site, substituted by Al for the Si-site, and substituted by O for the N-site, and subjected to structural optimization.
Figure 7:
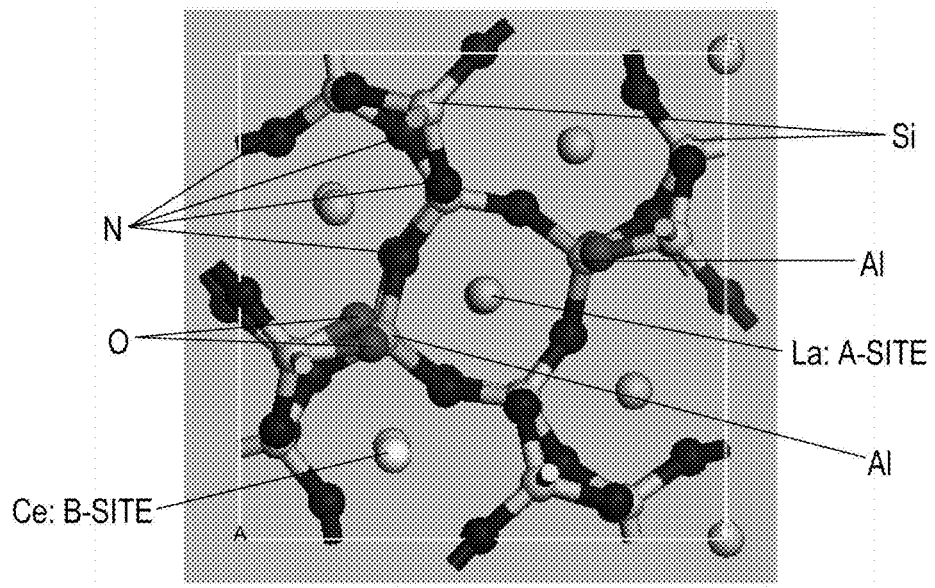
FIG. 7 is a diagram illustrating the 1×1×3 supercell structure of $La_3Si_6N_{11}:Ce$ substituted by Ce for La at the B-site, substituted by Al for the Si-site, and substituted by O for the N-site, and subjected to structural optimization.

Based on the above-mentioned viewpoint, in order to further reduce the symmetry, a crystal structure of $La_3Si_6N_{11}$:Ce substituted by Al for a part of the Si-site and by O for a part of the N-site, in the vicinity of Ce, was studied. For this crystal structure, crystal structure 3 substituted by Ce for La at the A-site and subjected to structural optimization is shown in FIG. 6; and crystal structure 4 substituted by Ce for La at the B-site and subjected to structural optimization is shown in FIG. 7. The distances between Ce and N atoms and standard deviations thereof in crystal structures 3 and 4 are shown in Table 1. The standard deviation values in crystal structures 3 and 4 are higher than that in crystal structure 1, which demonstrates that the symmetry of the ligands of Ce is decreased.

The above analytical results suggest a possibility that in a crystal structure $La_3Si_6N_{11}$:Ce substituted by Al for a part of the Si-site, in the vicinity of Ce or substituted by O for a part of the N-site, such as crystal structure 3 or 4, the equilibrium points of the 4f and 5d orbits shift due to the low symmetry of the ligands of Ce, and emission of light with a longer wavelength compared to known LSN:Ce yellow phosphors can be realized. In this case, in order to realize the emission of light with a longer wavelength compared to known LSN:Ce yellow phosphors, it is believed to be desirable that the amount of at least one selected from the group consisting of Al and O contained in the crystal phase is higher than that of Ce.

Furthermore, a crystal structure of $La_3Si_6N_{11}$:Ce substituted by Al for a part of the Si-site and having deficiency of the N-site, in the vicinity of Ce, was investigated. In order to adjust the valence in substitution by $Al^{3+}$ for of $Si^{4+}$, it is desirable to substitute three $Si^{4+}$ ions with three $Al^{3+}$ ions and simultaneously to cause a deficit of one $N^{3-}$ ion. A possibility is suggested that the symmetry of the ligands of Ce decreases by simultaneous occurrence of substitution for Si coordinated to a position near Ce with Al and a deficit of N, and emission of light with a longer wavelength compared to known LSN:Ce yellow phosphors can be realized.

In this case, in order to realize the emission of light with a longer wavelength compared to known LSN:Ce yellow phosphors, it is probably desirable that the molar number of at least Al is not lower than that of Ce. Furthermore, since charge compensation for the deficiency of N is possible by substituting three Si-sites with Al, it is probably desirable that the molar number of Al is 3 times or more the molar number of Ce.

The above results of crystal structure simulation demonstrate a possibility that a phosphor having any of (1) the crystal structure of an $La_3Si_6N_{11}$ crystal substituted by Ce for La at the B-site, (2) the crystal structure of an $La_3Si_6N_{11}$ crystal substituted by Ce for at least the A-site or the B-site of La and substituted by Al-O for a part of Si-N in the vicinity of Ce, and (3) the crystal structure of an $La_3Si_6N_{11}$ crystal substituted by Ce for at least the A-site or the B-site of La, substituted by Al for Si in the vicinity of Ce, and having a deficit of N can emit light at the long wavelength side compared to known LSN:Ce yellow phosphors.

The above simulation results suggest that the phosphor of Embodiment 1 is one example of the factors showing the emission of red light on the long wavelength side compared to known LSN:Ce yellow phosphors. That is, the above-described simulation results are merely one example and do not limit the crystal structure of the phosphor of Embodiment 1.

Light-Emitting Apparatus using Phosphor

The phosphor of Embodiment 1 can be used in light-emitting apparatuses. The light-emitting apparatus in this embodiment at least includes an excitation light source and a phosphor. The excitation light source emits light of a wavelength of 600 nm or less. The phosphor is the phosphor of Embodiment 1 that is irradiated with light emitted by the excitation light source and emits fluorescence having a wavelength longer than that of the light emitted by the excitation light source. The structure as described above can construct a light-emitting apparatus showing high quantum efficiency even under high output.

The light emitted by the excitation light source may have a wavelength of 500 nm or more and 600 nm or less. The phosphor of Embodiment 1 typically has a peak of the excitation spectrum at a wavelength of 500 nm or more and 600 nm or less and therefore can be efficiently excited. The light emitted by the excitation light source may have a wavelength of 200 nm or more and 500 nm or less. The phosphor of Embodiment 1 also absorbs excitation light at a wavelength of 500 nm or less. However, since light having a wavelength of 200 nm or less attenuates by absorption by air, the excitation light source desirably emits light of a wavelength of 200 nm or more. Examples of the excitation light source include LEDs and LDs.

The light-emitting apparatus of the embodiment may further include a second phosphor has a peak of the emission spectrum at a wavelength of 500 nm or more and 600 nm or less. The second phosphor is irradiated with light emitted by the excitation light source and thereby emits fluorescence having a wavelength longer than that of the light emitted by the excitation light source. As the second phosphor, for example, a phosphor containing a crystal phase having a chemical composition $Y_3Al_5O_{12}$:Ce (YAG:Ce) or a phosphor containing a crystal phase having a chemical composition $La_3Si_6N_{11}$:Ce (LSN:Ce) may be used.

Alternatively, a phosphor that emits yellow light is used as the second phosphor, and a third phosphor that emits green light may be further used. The third phosphor is irradiated with light emitted by the excitation light source and thereby emits fluorescence having a wavelength longer than that of the light emitted by the excitation light source. As the third phosphor, for example, a phosphor containing a chemical phase having a chemical composition $Lu_3Al_5O_{12}$:Ce (LuAG:Ce) or a phosphor containing a chemical phase having a chemical composition $Y_3(Al,Ga)_5N_{12}$:Ce (YAGG:Ce) may be used. Furthermore, the phosphor of Embodiment 1 may be excited with the light emitted by the second phosphor or the third phosphor. Herein, the green light refers to light located, in the CIE chromaticity coordinate value, within a range of $0.1 \leq x \leq 0.4$ and $0.5 \leq y \leq 0.8$. The yellow light refers to light located, in the CIE chromaticity coordinate value, within a range of $0.4 \leq x \leq 0.6$ and $0.4 \leq y \leq 0.6$.

The excitation light source and the second and third phosphors in the light-emitting apparatus including the phosphor of Embodiment 1 can be freely selected within the above-described ranges according to the use of the light-emitting apparatus. Accordingly, the light-emitting apparatus including the phosphor of Embodiment 1 is useful as not only a red light-emitting apparatus but also, for example, a white light-emitting apparatus. Specifically, a high-output light-emitting apparatus having high color rendering properties or a high-output light-emitting apparatus emitting light of light bulb color can be realized by combining an excitation light source emitting blue light, a phosphor emitting yellow light, and the red phosphor of the embodiment.

Embodiment 2

Figure 8:
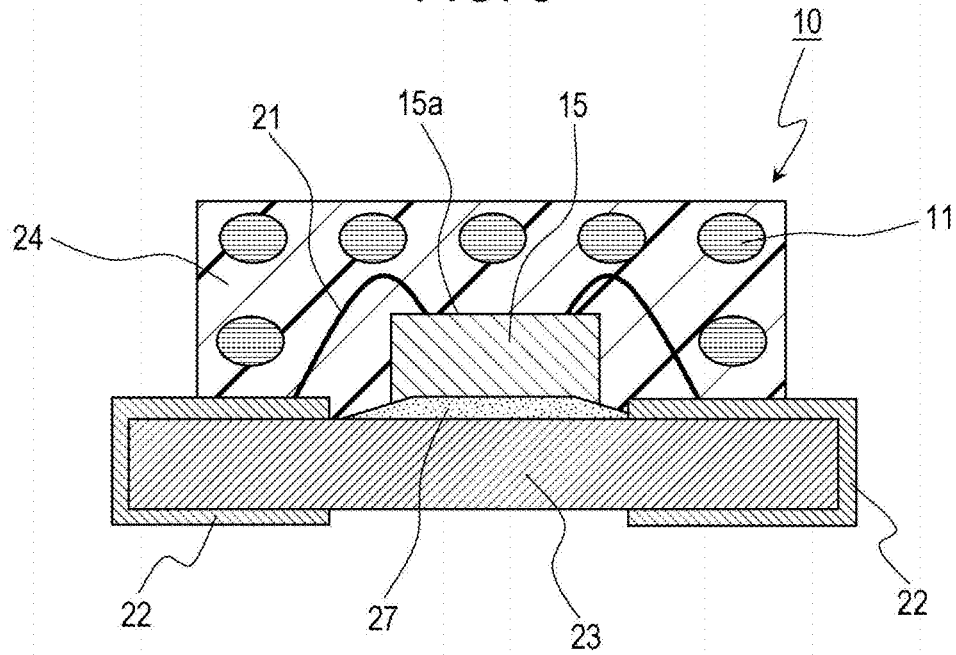
FIG. 8 is a schematic cross-sectional view of an LED light-emitting apparatus according to Embodiment 2.

In Embodiment 2, an LED light-emitting apparatus including an LED chip serving as a light emitting element as the light source will be described as an example of the light-emitting apparatus of the present disclosure. FIG. 8 is a schematic cross-sectional view illustrating an embodiment of an LED light-emitting apparatus according to Embodiment 2. As shown in FIG. 8, the LED light-emitting apparatus 10 includes a phosphor 11, an LED chip 15, and an LED sealing member 24 and may further include a support 23. The support 23 supports the LED chip 15. In this embodiment, the LED light-emitting apparatus 10 has a surface-mountable structure, and the support 23 is therefore a substrate.

The embodiment can be used in a high-brightness LED light-emitting apparatus. For example, the support 23 has high thermal conductivity such that the heat generated in the LED chip 15 can be efficiently released to the outside. For example, a ceramic substance made of alumina, aluminum nitride, or the like can be used as the support 23.

As the LED chip 15, for example, a chip that emits light in the ultraviolet to yellow region is used, and a chip that has a peak of the emission spectrum at a wavelength of 200 nm or more and 600 nm or less is used. Specifically, as the LED chip 15, for example, a yellow LED chip, a green LED chip, a blue LED chip, a violet LED chip, a near ultraviolet LED chip, or an ultraviolet LED chip can be used. On the support 23, the LED chip 15 is fixed to the support 23 with, for example, solder 27 in such a manner that the light emission surface 15a is not the surface in contact with the support 23. In addition, the LED chip 15 is electrically connected to electrodes 22 disposed to the support 23 via bonding wires 21. The LED chip 15 is covered with an LED sealing member 24.

In the LED sealing member 24, a silicone resin is used. The phosphor 11 is dispersed in the LED sealing member 24. As the silicone resin, silicone resins having structures prescribed by various chemical formulae used as sealing resins for semiconductor light emitting elements can be used. The silicone resin contains, for example, dimethyl silicone having high color fastness. In addition, for example, methylphenyl silicone having high heat resistance can be used as the silicone resin. The silicone resin may be a homopolymer prescribed by one chemical formula and having a main skeleton of siloxane bonds or may be a copolymer including structural units prescribed by two or more chemical formulae and having siloxane bonds or an alloy of two or more silicone polymers.

In this embodiment, the silicone resin in the LED sealing member 24 is in a cured state. Accordingly, the LED sealing member 24 is also in a cured state. As described below, the LED sealing member 24 can be produced using an uncured silicone resin. The silicone resin is generally a two-pack type resin of which curing is enhanced by mixing a main agent and a curing agent. However, a thermosetting silicone resin or an energy setting silicone resin, which cures by being irradiated with energy, such as light, can also be used. In the LED sealing member 24, a material other than the silicone resin may be used. For example, glass; resins, such as epoxy resins; and inorganic materials composed of ZnO may be used. The phosphor 11 may be disposed on the LED sealing member 24 in a form of a phosphor plate, without being dispersed in the LED sealing member 24.

In the examples described above, the LED chip is wire-bonded. The LED chip used in the embodiment may have another structure. That is, the LED chip used in the embodiment may be face-up mounted or may be flip-chip mounted. The LED chip used in the embodiment may include a light emission layer formed of a nitride semiconductor having a growing surface of a typical polar plane (c plane).

Overview of Phosphor

The phosphor 11 absorbs a part or the whole of the wavelength components of light (e.g., near ultraviolet light) in the near ultraviolet to yellow region emitted from the LED chip 15 and emits fluorescence. The wavelength of the light to be absorbed and the wavelength of the fluorescence are determined depending on the type of the fluorescent material contained in the phosphor 11. The phosphor 11 may be a phosphor mixture containing a plurality of phosphors of different colors so as to produce white light by color mixing of light. The phosphor 11 may be a phosphor mixture of a green phosphor and a red phosphor. As the red phosphor, the phosphor of Embodiment 1 is used.

As the green phosphor, for example, $M^H{}_2MgSi_2O_7:Eu^{2+}$ ($M^H$: at least one selected from the group consisting of Ba, Sr, and Ca), $SrSi_5AlO_2N_7:Eu^{2+}$, $SrSi_2O_2N_2:Eu^{2+}$, $BaAl_2O_4$:$Eu^{2+}$, $BaZrSi_3O_9:Eu^{2+}$, $M^H{}_2SiO_4:Eu^{2+}$ ($M^H$: at least one selected from the group consisting of Ba, Sr, and Ca), $BaSi_3O_4N_2:Eu^{2+}$, $Ca_8Mg(SiO_4)_4Cl_2:Eu^{2+}$, $Ca_3SiO_4Cl_2$:$Eu^{2+}$, and $\beta$-$SiAlON:Eu^{2+}$ can be used.

As another aspect, the phosphor 11 may be a phosphor mixture of a yellow phosphor and a red phosphor. As the red phosphor, the phosphor of Embodiment 1 is used. As the yellow phosphor, for example, $Y_3Al_5O_{12}:Ce^{3+}$, $CaSi_2O_2N_2$:$Eu^{2+}$, $(Ba,Sr)Si_2O_2N_2:Eu^{2+}$, $Ca_3Sc_2Si_3O_{12}:Ce^{3+}$, $CaSc_2O_4$:$Ce^{3+}$, $\alpha$-$SiAlON:Eu^{2+}$, and $La_3Si_6N_{11}:Ce^{3+}$ can be used.

The particle diameter of the phosphor 11 is, for example, 1 μm or more and 80 μm or less. In the present specification, the term "particle diameter" refers to that represented by the circle equivalent diameter by microscopy.

The phosphor 11 is contained in the LED sealing member 24 at a rate of, for example, 3 parts by weight or more and 70 parts by weight or less based on 100 parts by weight of the sealing member. If the content of the phosphor 11 is less than 3 parts by weight, fluorescence with sufficient intensity cannot be obtained, and thereby it may be impossible to realize the LED light-emitting apparatus 10 emitting light of a desired wavelength. The weight ratio of the phosphors that emit light of the respective colors used in the phosphor 11 can be appropriately determined according to the desired tone of white light and the emission intensity of each phosphor. The LED light-emitting apparatus can also be constituted so as to emit light of a color other than white by using, as the phosphor 11, only the red phosphor of Embodiment 1 or combination with a phosphor of another color.

The phosphor other than the red phosphor of Embodiment 1 can be produced in accordance with a known method. Specifically, in production of an oxide phosphor, a compound that becomes an oxide by firing, such as hydroxides, oxalates, and nitrates, or an oxide can be used as a raw material. Herein, in order to accelerate the reaction, a small amount of a fluoride (e.g., calcium fluoride) or a chloride (e.g., calcium chloride) can be added. The phosphor is produced by mixing the above-mentioned raw materials and firing the mixture.

The method of mixing the raw materials may be wet blending in a solvent or dry blending of dry powders. A machine commonly used industrially, such as a ball mill, a medium stirring mill, a planetary mill, a vibration mill, a jet mill, a V-type mixer, or a stirrer, can be used. The phosphor raw materials are fired in the atmosphere or under a reducing atmosphere within a temperature range of 1100° C. to 1700° C. for about 1 to 50 hours. As the furnace for the firing, a furnace that is usually used industrially can be used. For example, a continuous furnace, such as a pusher furnace; a batch type electric or gas furnace; or a pressure firing furnace for spark plasma sintering (SPS) or hot isostatic pressing (HIP) sintering can be used. The resulting phosphor powder is pulverized again with, for example, a ball mill or a jet mill and is washed or sorted as needed to adjust the particle size distribution and fluidity of the phosphor powder.

Embodiment 3

Figure 9:
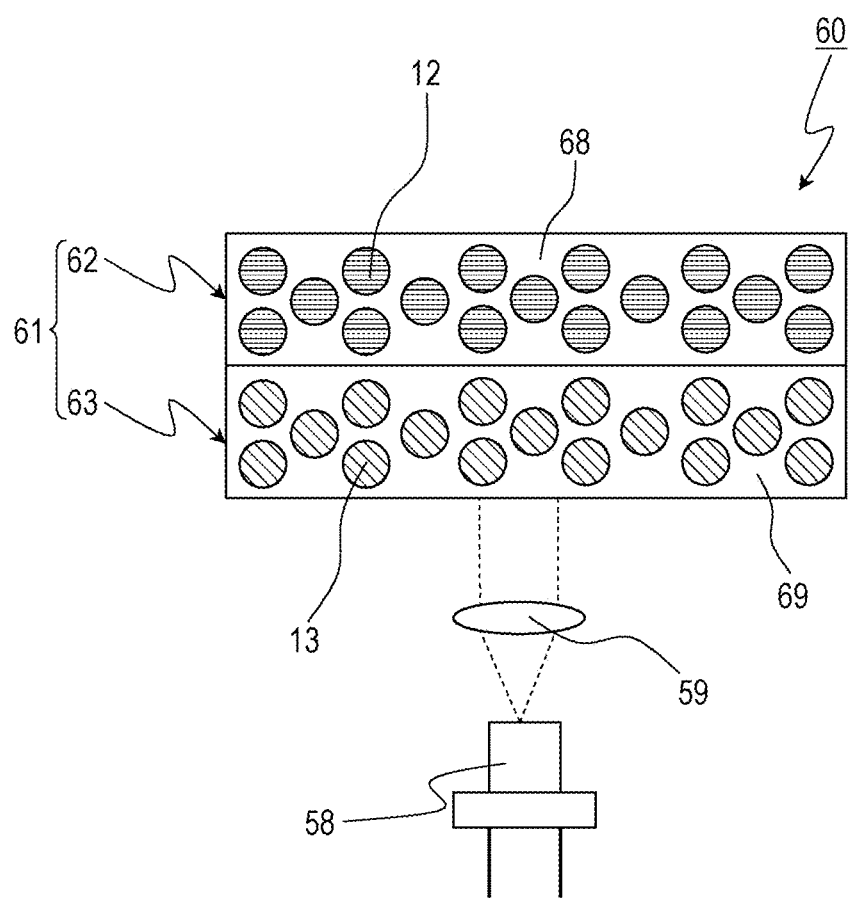
FIG. 9 is a schematic cross-sectional view of an LD light-e ng apparatus according to Embodiment 3.

In Embodiment 3, an LED light-emitting apparatus including an LD serving as a light emitting element as the light source will be described as an example of the light-emitting apparatus of the present disclosure. FIG. 9 schematically illustrates the structure of an LD light-emitting apparatus 60 according to Embodiment 3. The LD light-emitting apparatus 60 includes an LD element 58 and a wavelength conversion member 61. The wavelength conversion member 61 contains a phosphor. The phosphor converts the light emitted from the LD element 58 to light having a longer wavelength.

The LD element 58 can emit light with a high light power density compared to an LED. Accordingly, the use of the LD element 58 allows to constitute a higher-output LD light-emitting apparatus 60. The power density of the light emitted from the LD element 58 and irradiating the phosphor is, for example, 0.5 W/mm$^2$ or more from the viewpoint of increasing the output of the LD light-emitting apparatus 60. The power intensity of the light irradiating the phosphor may be 2 W/mm$^2$ or more, 3 W/mm$^2$ or more, or 10 W/mm$^2$ or more. However, a too high power density of the light irradiating the phosphor increases the amount of heat generated by the phosphor and has a risk of adversely affecting the LD light-emitting apparatus 60. Accordingly, the power density of the light irradiating the phosphor may be 150 W/mm$^2$ or less, 100 W/mm$^2$ or less, 50 W/mm$^2$ or less, or 20 W/mm$^2$ or less.

The LD element 58 may be any LD element that emits light of a wavelength capable of exciting the phosphor. For example, an LD element emitting violet light, an LD element emitting blue light, an LD element emitting green light, or an LD element emitting yellow light can be used. In this embodiment, an LD element 58 emitting blue light will be described. Throughout the present specification, the term "blue light" refers to light of which the peak wavelength is 420 nm or more and less than 480 nm. In general, the LD element 58 emitting blue light has high emission efficiency compared to an LD element emitting ultraviolet light, and an emission peak wavelength of 445 nm gives the highest light emission efficiency. The emission peak wavelength of the LD element 58 may be 425 nm or more or 430 nm or more. At the same time, the emission peak wavelength of the LD element 58 may be 475 nm or less or 470 nm or less.

The LD element 58 may be composed of a single LD or may be composed of a plurality of optically connected LDs. The LD element 58 may include, for example, a light emission layer formed from a nitride semiconductor having a growing surface that is a non-polar or semi-polar plane.

The phosphor of the wavelength conversion member 61 contains the red phosphor of Embodiment 1. The wavelength conversion member 61 may further contain a phosphor other than the red phosphor of Embodiment 1 according to the desired color of the light emitted by the light-emitting apparatus. For example, when the wavelength conversion member 61 further contains a yellow phosphor and a green phosphor, the LD light-emitting apparatus 60 can be constituted as a white light-emitting apparatus. As the yellow phosphor and the green phosphor, the examples mentioned in Embodiment 2 can be used. The wavelength conversion member 61 may be composed of a single wavelength conversion layer in which a plurality of phosphors are mixed or may be composed of stacked two or more wavelength conversion layers each containing one or more phosphors. In this embodiment, in particular, a case of using a wavelength conversion member 61 having a stacked structure composed of a first phosphor layer 62 constituted of a red phosphor 12 and a second phosphor layer 63 constituted of a yellow phosphor 13 will be described.

The first phosphor layer 62 and the second phosphor layer 63 are constituted by using binders 68 and 69, respectively. The binders 68 and 69 are, for example, a resin, glass, or a medium, such as a transparent crystal. The binders 68 and 69 may be the same material or different materials. Each of the phosphor layers may be constituted of phosphor particles only.

Between the wavelength conversion member 61 and the LD element 58, an incident optical system 59 guiding the light of the LD element 58 to the second phosphor layer 63 may be disposed. The incident optical system 59 may include, for example, a lens, mirror, or an optical fiber.

Subsequently, operation of the LD light-emitting apparatus 60 will be described. Blue light emitted from the LD element 58 passes through the incident optical system 59 and enters the second phosphor layer 63 of the wavelength conversion member 61. This incident light excites a plurality of molecules of the yellow phosphor 13 in the second phosphor layer 63, and yellow light is emitted. Blue light emitted from the LD element 58 and passed through the second phosphor layer 63 without being absorbed enters the first phosphor layer 62. This incidence excites a plurality of molecules of the red phosphor 12 in the first phosphor layer 62, and red light is emitted. In addition, the yellow light radiated from the second phosphor layer 63 enters the first phosphor layer 62. A part of this incident light may excite a plurality of molecules of the red phosphor 12 in the first phosphor layer 62, and red light may be emitted. Blue light emitted from the LD element 58 and passed through the second phosphor layer 63 and the first phosphor layer 62 without being absorbed is radiated to the outside. These red light, yellow light, and blue light mix to white light.

The thickness of each of the phosphor layers may be adjusted such that the blue light emitted from the LD element 58 does not pass through the first phosphor layer 62 and the yellow light radiated from the second phosphor layer 63 does not pass through the first phosphor layer 62. In this case, only the red light is radiated to the outside. As another aspect, the green phosphor described in Embodiment 2 may be used instead of the yellow phosphor 13 used in the second phosphor layer 63.

Embodiment 4

Figure 10:
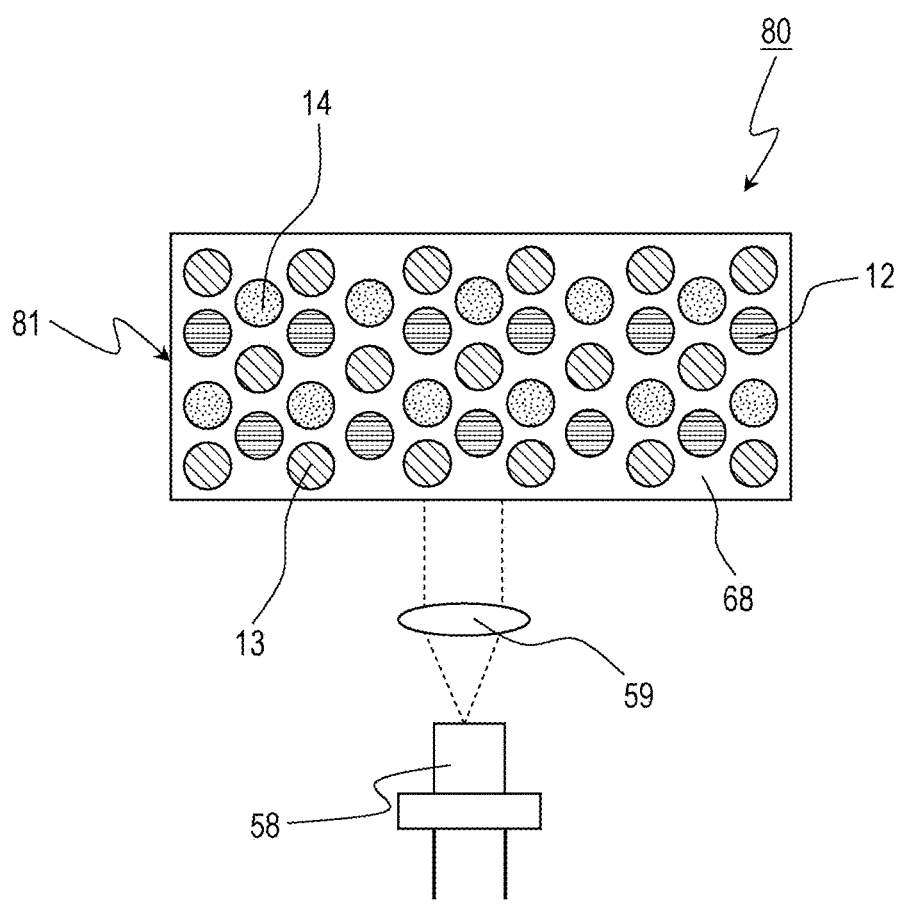
FIG. 10 is a schematic cross-sectional view of an LD light-emitting apparatus according to Embodiment 4.

In Embodiment 4, an LED light-emitting apparatus including an LD serving as a light emitting element as the light source will be described as an example of the light-emitting apparatus of the present disclosure. FIG. 10 schematically illustrates the structure of an LD light-emitting apparatus 80 according to Embodiment 4. The same members as in Embodiment 3 are assigned with the same reference numerals, and descriptions thereof are omitted. The LD light-emitting apparatus 80 includes an LD element 58 and a wavelength conversion member 81.

The wavelength conversion member 81 contains a phosphor. The phosphor converts the light emitted from the LD element 58 to light having a longer wavelength. The wavelength conversion member 81 includes a wavelength conversion layer in which a red phosphor 12 and at least one selected from the group consisting of a yellow phosphor 13 and a green phosphor 14 are mixed. As the red phosphor 12, the phosphor of Embodiment 1 is used. As the yellow phosphor and the green phosphor, the examples mentioned in Embodiment 2 can be used. In this embodiment, in particular, a case where the wavelength conversion member 81 is a phosphor layer formed by mixing three phosphors, a red phosphor 12, a yellow phosphor 13, and a green phosphor 14, will be described. The mixing ratio of the three phosphors can be appropriately adjusted according to the desired tone of white light and the emission intensity of each phosphor.

The phosphor layer as the wavelength conversion member 81 is constituted by using a binder 68. The binder 68 is, for example, a resin, glass, or a medium, such as a transparent crystal. The binder 68 may be constituted of a single material or may be constituted of different materials depending on positions in the phosphor layer. The phosphor layer may be constituted of phosphor particles only.

The blue light emitted from the LD element 58 passes through an incident optical system 59 and is converted by the red phosphor 12, the yellow phosphor 13, and the green phosphor 14 in the wavelength conversion member 81 to red light, yellow light, and green light, respectively. The blue light emitted from the LD element 58 and not absorbed by the phosphors and the red light, the yellow light, and the green light converted by the red phosphor 12, the yellow phosphor 13, and the green phosphor 14, respectively, mix to white light.

As described above, in the light-emitting apparatuses of Embodiment 2 to 4, since the red phosphor of Embodiment 1 is used, the quantum efficiency under high output can be improved than before. Furthermore, when the light-emitting apparatus is constituted as a white light-emitting apparatus, high color rendering properties and color reproducibility can be realized.

Embodiment 5

Figure 11:
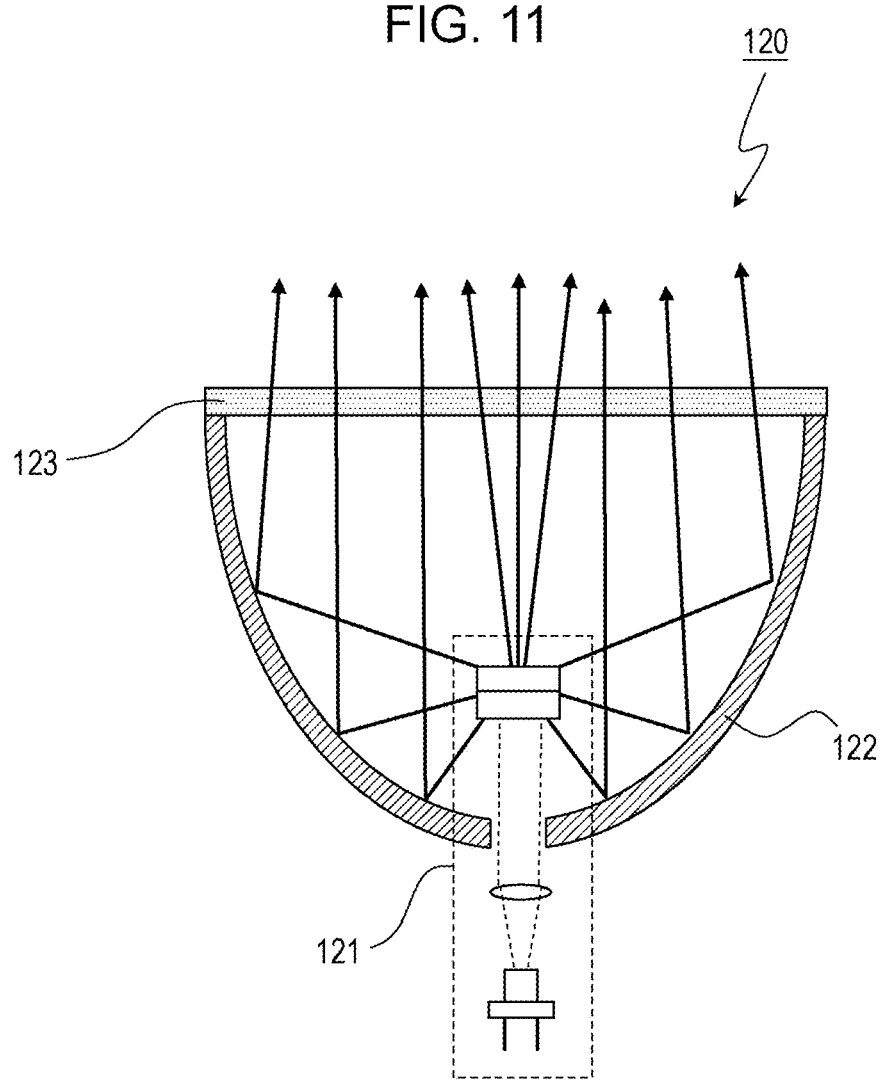
FIG. 11 is a schematic cross-sectional view of a lighting system according to Embodiment 5.

In Embodiment 5, an example of a lighting system of the present disclosure will be described. FIG. 11 schematically illustrates the structure of a lighting system 120 according to Embodiment 5. The lighting system 120 includes a light source 121 and a light-emitting optical system 122 guiding the light emitted by the light source 121 forward. In order to adjust the color of light from the light source, a wavelength cut filter 123 absorbing or reflecting the light from the light source may be disposed. The light source 121 contains the red phosphor of Embodiment 1. Alternatively, the light source 121 may be the light-emitting apparatus 10, 60, or 80 of Embodiments 2 to 4. The light-emitting optical system 122 may be, for example, a reflector. The light-emitting optical system 122 may include, for example, a film of a metal, such as Al or Ag, or an Al film having a protective film formed on a surface.

In the lighting system of Embodiment 5, since the red phosphor of Embodiment 1 is used, the quantum efficiency under high output can be improved compared to known lighting systems. Furthermore, when the lighting system is constituted as a white lighting system, high color rendering properties and color reproducibility can be realized.

Embodiment 6

Figure 12:
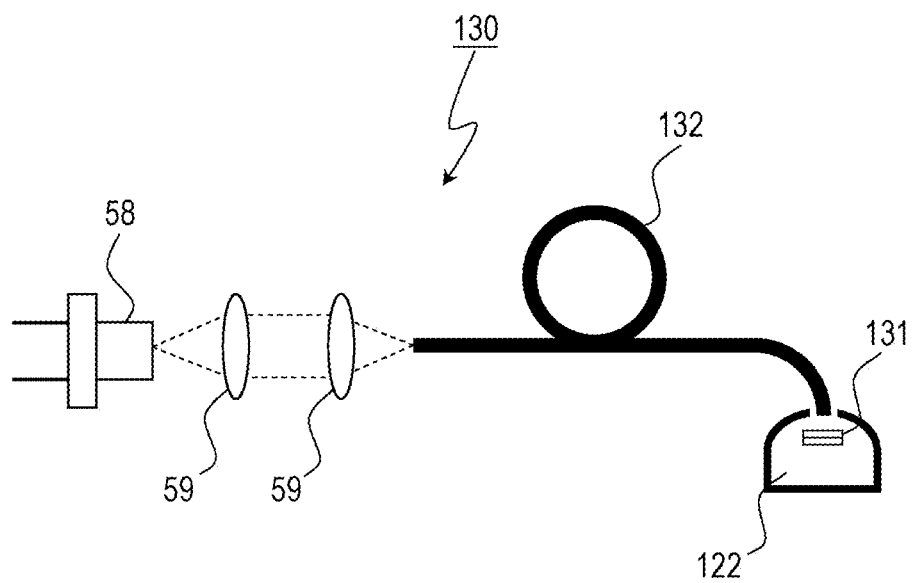
FIG. 12 is a schematic cross-sectional view of a lighting system according to Embodiment 6.

In Embodiment 6, a lighting system using an optical fiber will be described as an example of the lighting system of the present disclosure. FIG. 12 schematically illustrates the structure of a lighting system 130 according to Embodiment 6. The lighting system 130 includes an LD element 58, incident optical systems 59, an optical fiber 132, a wavelength conversion member 131, and a light-emitting optical system 122.

The light emitted by the LD element 58 passes through the incident optical systems 59 and is guided to the optical fiber 132. The optical fiber 132 guides the light to an emission part. The emission part includes, for example, the wavelength conversion member 131 and the light-emitting optical system 122. The wavelength conversion member 131 contains the red phosphor of Embodiment 1. The wavelength conversion member 131 may be the wavelength conversion member 61 or 81 of Embodiments 3 and 4. Although the wavelength conversion member 131 may be disposed on the emission side than the optical fiber 132 as shown in FIG. 12, it may be disposed on the incidence side (e.g., between the LD element 58 and the incident optical system 59 or between the incident optical system 59 and the optical fiber 132) than the optical fiber 132.

In the lighting system of Embodiment 6, the direction of light irradiation can be simply changed by using the optical fiber.

Since the red phosphor of Embodiment 1 is used, the quantum efficiency under high output can be improved compared to known lighting systems. Furthermore, when the lighting system is constituted as a white lighting system, high color rendering properties and color reproducibility can be realized.

Embodiment 7

Figure 13:
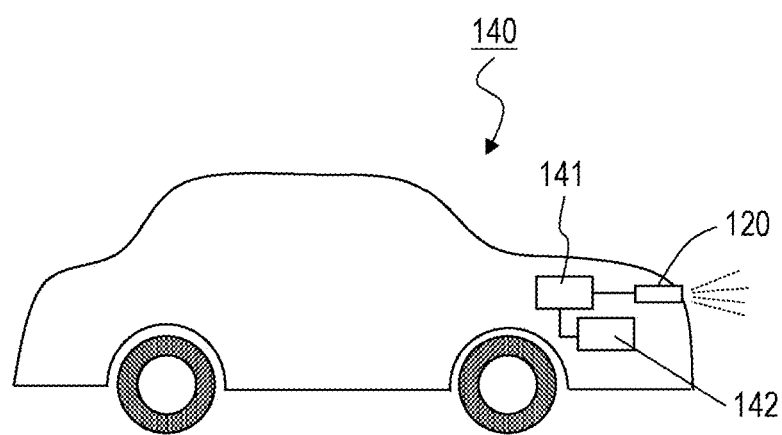
FIG. 13 is a schematic cross-sectional view of a vehicle according to Embodiment 7.

In Embodiment 7, a vehicle including a lighting system will be described as an application example of the lighting system of the present disclosure. FIG. 13 schematically illustrates the structure of a vehicle 140 according to Embodiment 7. The vehicle 140 includes a head lamp for the vehicle of the lighting system 120 of Embodiment 5 and a power supply source 141. The vehicle 140 may be rotationally driven by a driving force, such as an engine and may include a power generator 142 that generates power. The power generated by the power generator 142 may be stored in the power supply source 141. The power supply source 141 may be a rechargeable secondary battery. The lighting system 120 is turned on by the power from the power supply source 141. The vehicle 140 is, for example, a car, a motorcycle, or a special vehicle. In addition, the vehicle 140 may be an engine car, an electric car, or a hybrid car.

In the vehicle of Embodiment 7, since the red phosphor of Embodiment 1 is included in the head lamp for the vehicle, the lamp can light forward brightly more than before under high output. Furthermore, when the lamp is constituted as a white lighting system, high color rendering properties and color reproducibility can be realized.

EXAMPLES

The present disclosure will now be described in detail, but the present disclosure is not limited to the following examples.

Examples 1 to 4 and Comparative Example 1

A method of producing a phosphor will now be shown. As starting materials, a LaN powder, a $Si_3N_4$ powder, an AlN powder, and a $CeF_3$ powder were prepared. The LaN powder, the $Si_3N_4$ powder, and the $CeF_3$ powder were weighed so as to give a composition represented by the formula $La_{2.91}Ce_{0.09}Si_6N_{11}$ and were mixed. However, the LaN powder was weighed in an amount higher by 24% than the theoretical value. To this powder mixture, the AlN powder was added in an amount shown in Table 2, followed by further mixing. In Comparative Example 1, the AlN powder was not added. The mixing was performed by dry blending using a mortar in a glove box under a nitrogen atmosphere. The mixed raw material powders were put in a boron nitride crucible. The raw material powders were fired in a 0.5 MPa nitrogen atmosphere at 1900° C. for 2 hours. The sample after the firing was washed in a 10% nitric acid solution for 1 hour. The phosphors of Examples 1 to 4 and Comparative Example 1 were produced from the starting materials shown in Table 2 according to the above method.

TABLE 2

|  | LaN | $Si_3N_4$ | AlN | $CeF_3$ | x | Emission peak wavelength | Excitation peak wavelength |
| --- | --- | --- | --- | --- | --- | --- | --- |
| Example 1 | 1.316 g | 0.659 g | 0.096 g | 0.042 g | 0.09 | 642 nm | 540 nm |
| Example 2 | 1.206 g | 0.604 g | 0.265 g | 0.038 g | 0.09 | 642 nm | 537 nm |
| Example 3 | 1.113 g | 0.557 g | 0.407 g | 0.035 g | 0.09 | 642 nm | 539 nm |
| Example 4 | 0.932 g | 0.467 g | 0.682 g | 0.030 g | 0.09 | 641 nm | 539 nm |
| Comparative Example 1 | 1.380 g | 0.691 g | 0 g | 0.044 g | 0.09 | 536 nm | 450 nm |

Comparative Example 2

As starting materials, a $Ca_3N_2$ powder, a $Si_3N_4$ powder, an AlN powder, and a EuN powder were prepared. The $Ca_3N_2$ powder, the $Si_3N_4$ powder, the AlN powder, and the EuN powder were weighed so as to give a composition represented by the formula $Ca_{0.97}Eu_{0.03}AlSiN_3$ and were mixed. The mixing was performed by dry blending using a mortar in a glove box under a nitrogen atmosphere. The mixed raw material powders were put in a boron nitride crucible. The raw material powders were fired in a 0.5 MPa nitrogen atmosphere at 1600° C. for 2 hours. The sample after the firing was washed in a 10% nitric acid solution for 1 hour. The phosphor of Comparative Example 2 represented by CASN:Eu was produced according to the above method.

Evaluation of Emission and Excitation Spectra

Figure 14:
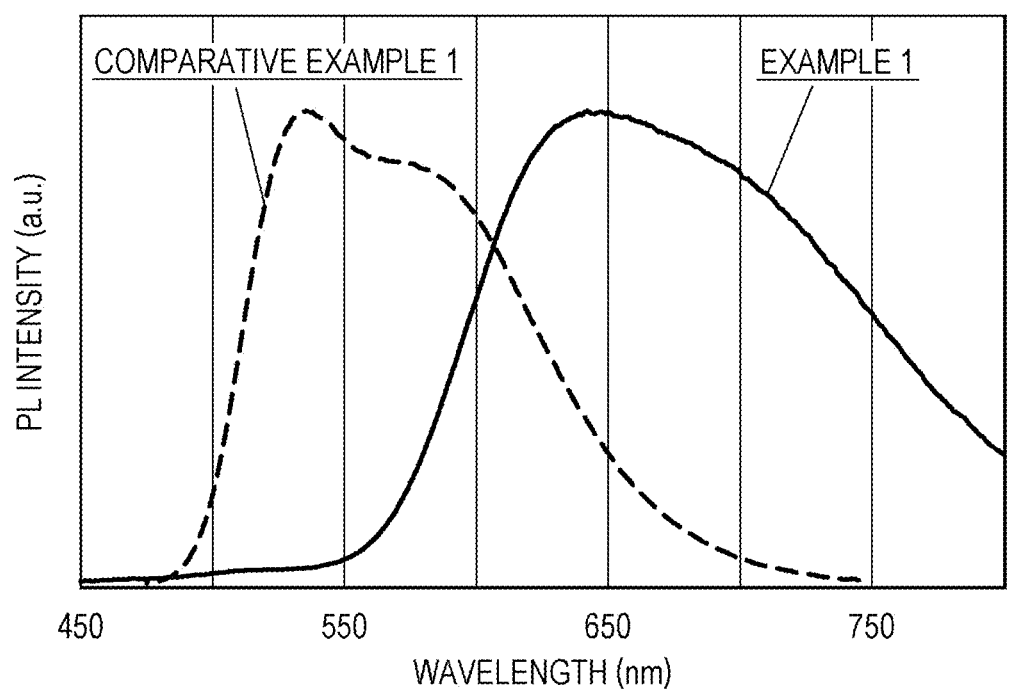
FIG. 14 shows emission spectra of Example 1 and Comparative Example 1.
Figure 15:
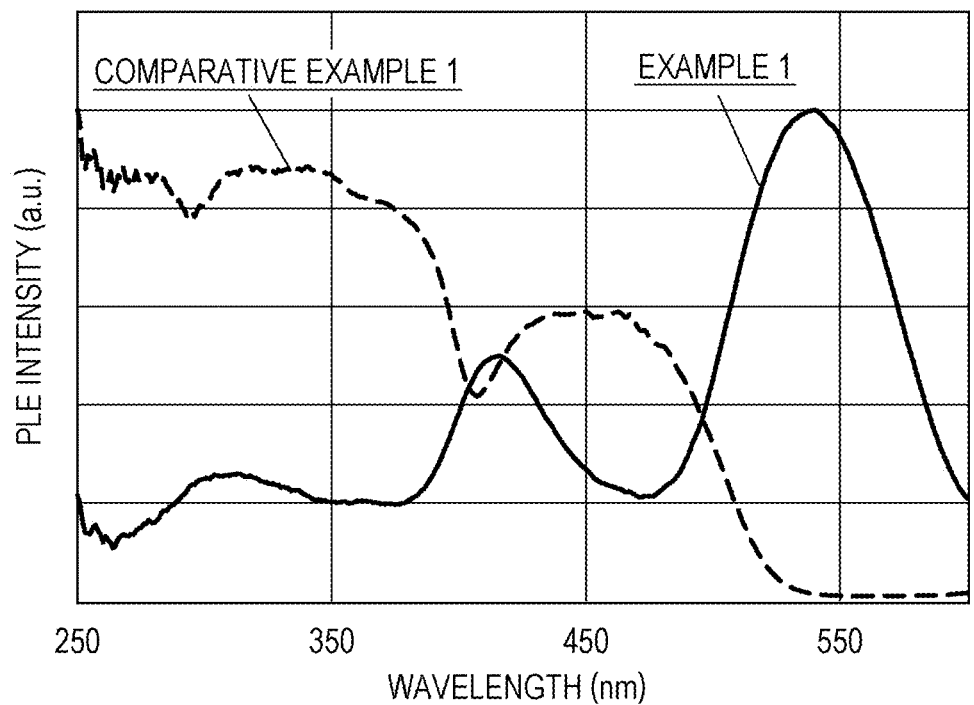
FIG. 15 shows excitation spectra of Example 1 and Comparative Example 1.

The emission spectra and the excitation spectra of Examples 1 to 4 and Comparative Example 1 were measured with a spectrofluorophotometer (FP-6500, manufactured by JASCO Corporation). FIG. 14 shows the emission spectra of Example 1 and Comparative Example 1, and FIG. 15 shows the excitation spectra. Table 2 shows emission peak wavelengths in a wavelength range of 450 to 800 nm and excitation peak wavelengths in a wavelength range of 400 to 600 nm. As the excitation light source, a Xe ramp was used.

The emission spectra were measured using the excitation peak wavelength of each sample shown in Table 2 as the wavelength of the excitation light source. The excitation spectra were measured using the emission peak wavelength of each sample shown in Table 2 as the monitor wavelength.

In Comparative Example 1 not containing AlN in the starting material, yellow light having an emission peak wavelength of 536 nm was emitted, and the excitation peak wavelength was 450 nm. It is generally known that a phosphor that is a crystal represented by $La_3Si_6N_{11}$ and doped with Ce has an emission peak (about 535 nm) on the short wavelength side and an emission peak (about 580 nm) on the long wavelength side. This almost agrees with the emission peak on the short wavelength side and an emission peak on the long wavelength side in the phosphor of Japanese Patent No. 4459941. In addition, the position of the excitation peak wavelength also almost agrees with Japanese Patent No. 4459941.

In contrast, in Examples 1 to 4, red light having an emission peak wavelength of about 640 nm was emitted. It was also demonstrated that in Examples 1 to 4, an excitation peak appears at a wavelength of about 540 nm. From the above, it is obvious that light emission characteristics in Examples 1 to 4 are different from those in Comparative Example 1. In Examples 1 to 4, the excitation spectrum further had a peak in a wavelength range of 350 nm or more and less than 500 nm.

Evaluation of Emission Lifetime

Figure 16:
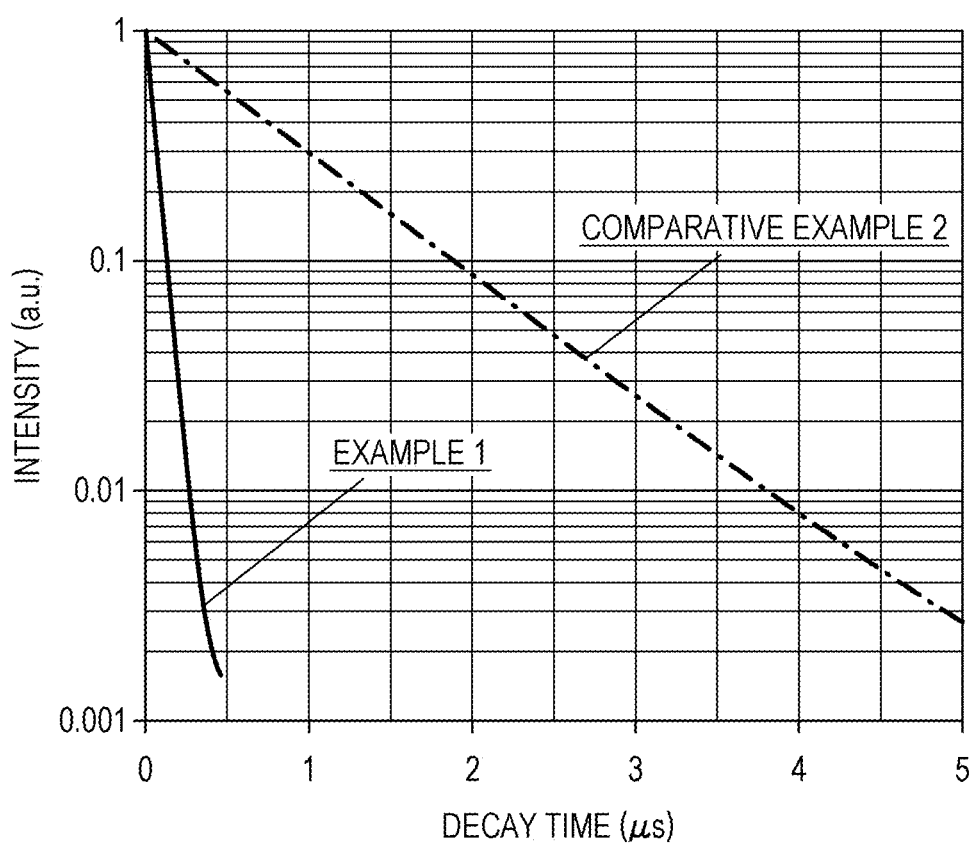
FIG. 16 shows afterglow spectra of Example 1 and Comparative Example 2.

The emission lifetimes in Examples 1 to 4 and Comparative Examples 1 and 2 were measured with a fluorescence lifetime measuring apparatus (Quantaurus-Tau compact fluorescence lifetime spectrometer, manufactured by Hamamatsu Photonics K.K.). FIG. 16 shows afterglow spectra of Example 1 and Comparative Example 2 by plotting changes in emission intensity with respect to the time after blocking the excitation light. Table 3 shows 1/e emission lifetimes in Examples 1 to 4 and Comparative Examples 1 and 2.

TABLE 3

|  | 1/e Emission lifetime |
|---|---|
| Example 1 | 54 ns |
| Example 2 | 55 ns |
| Example 3 | 54 ns |
| Example 4 | 53 ns |
| Comparative Example 1 | 42 ns |
| Comparative Example 2 | 820 ns |

The 1/e emission lifetime in Example 1 was 54 ns. In Examples 1 to 4 and Comparative Example 1, the 1/e emission lifetimes were each about 50 ns and were verified to be 100 ns or less. It is known that the emission lifetime of Ce is generally about 10 to 100 ns. Accordingly, the light emission in Examples 1 to 4 and Comparative Example 1 is probably originated from Ce.

In contrast, the emission lifetime of CASN:Eu of Comparative Example 2 was 820 ns. The emission lifetime affects the brightness saturation characteristics. It is known that a phosphor containing Eu decreases the quantum efficiency under high output excitation and thereby readily causes brightness saturation, compared to a phosphor containing Ce. It is believed that the phosphors in Examples 1 to 4 and Comparative Example 1 have considerably low emission lifetime values compared to that of CASN:Eu, and therefore the brightness thereof is hardly saturated. Accordingly, the phosphors of Examples 1 to 4 and Comparative Example 1 can realize high-output light-emitting devices by being combined with high-output excitation light sources.

Evaluation of Crystal Structure

The powder X-ray diffraction patterns of Examples 1 to 4 and Comparative Example 1 were measured with an X-ray diffraction measuring apparatus (RINT2100, manufactured by Rigaku Corporation). The measurement was performed using Cu-Kα radiation under conditions shown in Table 4.

TABLE 4

| Starting angle | Ending angle | Sampling width | Scanning speed | Tube voltage | Tube current | Diffusion slit | Scattering slit | Light-receiving slit |
|---|---|---|---|---|---|---|---|---|
| 10° | 60° | 0.02° | 4°/min | 40 kV | 40 mA | 1° | 1° | 0.15 mm |

Figure 17:
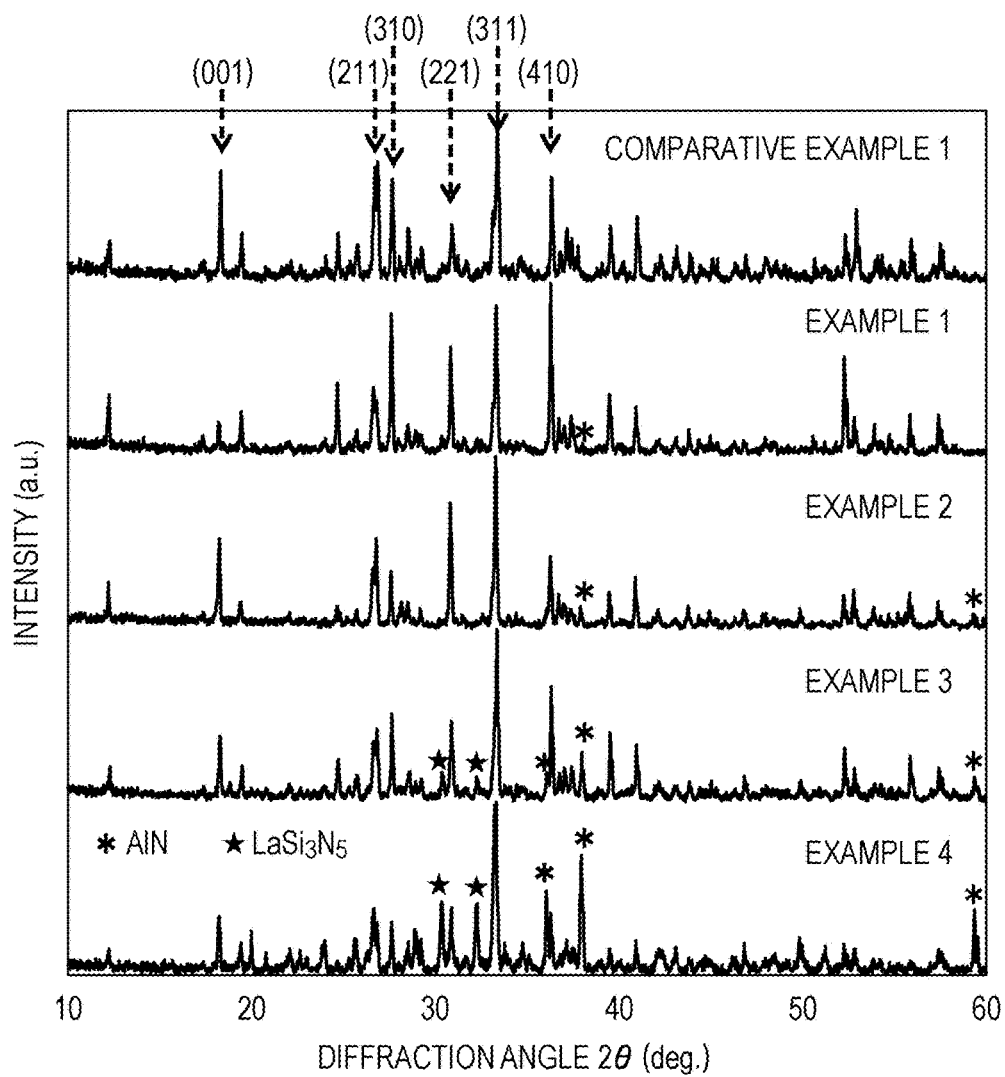
FIG. 17 shows XRD diffraction patterns of Examples 1 to 4 and Comparative Example 1.

The resulting X-ray diffraction patterns are shown in FIG. 17. FIG. 17 demonstrates that the X-ray diffraction patterns in Examples 1 to 4 slightly shifted to the low angle side with respect to the X-ray diffraction pattern obtained in Comparative Example 1, but both are almost the same.

In the resulting diffraction peaks, six diffraction peaks corresponding to the crystal form of $La_3Si_6N_{11}$ are defined as peaks 1 to 6 from the low angle side, and Table 5 shows the values of 2θ of the diffraction peaks.

TABLE 5

|  | Peak 1 | Peak 2 | Peak 3 | Peak 4 | Peak 5 | Peak 6 |
|---|---|---|---|---|---|---|
| Example 1 | 18.20° | 26.62° | 27.60° | 30.84° | 33.30° | 36.26° |
| Example 2 | 18.24° | 26.76° | 27.60° | 30.82° | 33.28° | 36.24° |
| Example 3 | 18.28° | 26.80° | 27.64° | 30.88° | 33.36° | 36.30° |
| Example 4 | 18.24° | 26.62° | 27.64° | 30.88° | 33.30° | 36.04° |
| Comparative Example 1 | 18.32° | 26.84° | 27.68° | 30.90° | 33.38° | 36.30° |

Table 5 demonstrates that the X-ray diffraction pattern of each of the resulting phosphors has diffraction peaks, corresponding to the peaks 1 to 6, in (1) 2θ: 17.8° or more and 18.8° or less, (2) 2θ: 26.2° or more and 27.2° or less, (3) 2θ: 27.2° or more and 28.2 or less, (4) 2θ: 30.5° or more and 31.5 or less, (5) 2θ: 32.8° or more and 33.8° or less, and (6) 2θ: 35.8° or more and 36.8° or less. The plane indices indicated by the peaks 1 to 6 were (001), (211), (310), (221), (311), and (410), respectively. As shown in FIG. 17, the diffraction intensities of the diffraction peaks corresponding to AlN and $LaSi_3N_5$ increased with the charged amount of AlN. Regarding AlN, it is probably due to the remaining blended AlN in an unreacted state. Regarding $LaSi_3N_5$, it is probably due to the shift from the stoichiometry composition of the $La_3Si_6N_{11}$ crystal to readily generate a $LaSi_3N_5$ phase.

The space group of the phosphor of Example 1 was analyzed with a single X-ray structure analyzer (VariMax, manufactured by Rigaku Corporation). The result demonstrates that the space group is tetragonal. This suggests that the crystal structures of Examples 1 to 4 and Comparative Example 1 are almost the same as that of the crystal represented by the formula $La_3Si_6N_{11}$.

Examples 5 to 10

A method of producing a phosphor will now be shown. As starting materials, a LaN powder, a $Si_3N_4$ powder, an AlN powder, and a CeN powder were prepared. The LaN powder, the $Si_3N_4$ powder, and the CeN powder were weighed so as to give a composition represented by the formula $La_{3-x}Ce_xSi_6N_{11}$ and were mixed. However, the LaN powder was weighed in an amount higher by 24% than the theoretical value. To this powder mixture, the AlN powder was added, followed by further mixing. The mixing was performed by dry blending using a mortar in a glove box under a nitrogen atmosphere. The mixed raw material powders were put in a boron nitride crucible. The raw material powders were fired in a 0.5 MPa nitrogen atmosphere at 1900° C. for 2 hours. The sample after the firing was washed in a 10% nitric acid solution for 1 hour. The phosphors of Examples 5 to 10 were produced from the starting materials shown in Table 6 according to the above method.

TABLE 6

|  | LaN | $Si_3N_4$ | AlN | CeN | x | Emission peak wavelength | Excitation peak wavelength |
| --- | --- | --- | --- | --- | --- | --- | --- |
| Example 5 | 1.028 g | 0.505 g | 0.074 g | 0.004 g | 0.015 | 624 nm | 534 nm |
| Example 6 | 1.024 g | 0.505 g | 0.074 g | 0.008 g | 0.03 | 630 nm | 534 nm |
| Example 7 | 1.007 g | 0.505 g | 0.074 g | 0.025 g | 0.09 | 644 nm | 536 nm |
| Example 8 | 0.991 g | 0.505 g | 0.074 g | 0.042 g | 0.15 | 644 nm | 540 nm |
| Example 9 | 0.974 g | 0.505 g | 0.074 g | 0.058 g | 0.21 | 650 nm | 541 nm |
| Example 10 | 0.957 g | 0.504 g | 0.074 g | 0.075 g | 0.27 | 653 nm | 542 nm |

Evaluation of Emission and Excitation Spectra

Figure 18:
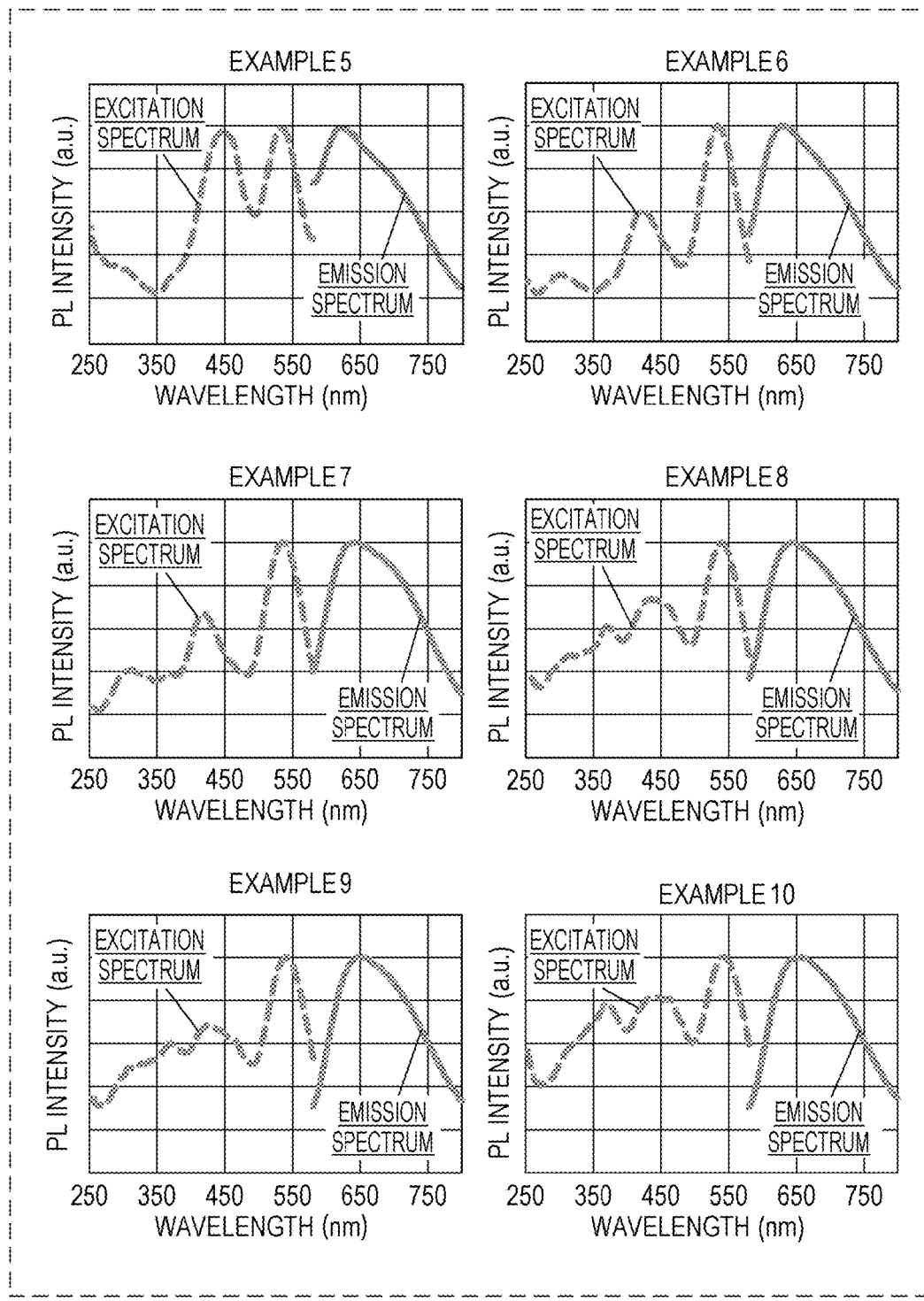
FIG. 18 shows emission spectra and excitation spectra of Examples 5 to 10.

The emission spectra and the excitation spectra of Examples 5 to 10 were measured with a spectrofluorophotometer (FP-6500, manufactured by JASCO Corporation). FIG. 18 shows the emission spectra and the excitation spectra of Examples 5 to 10. As the excitation light source, a Xe ramp was used. The emission spectra were measured using the excitation peak wavelength of each sample shown in Table 6 as the wavelength of the excitation light source. The excitation spectra were measured using the emission peak wavelength of each sample shown in Table 6 as the monitor wavelength. In all samples of Examples 5 to 10, emission of red light having an emission peak wavelength of 600 nm or more was observed. The resulting emission peak wavelengths were 624 to 653 nm.

In all samples of Examples 5 to 10, excitation peak wavelengths were observed at a wavelength of 500 nm or more. The resulting excitation peak wavelengths were 534 to 542 nm. An increase in the Ce concentration (the value of x) in a phosphor increases the overlap of the wave functions of excitation levels of Ce atoms. The excitation level energy width then increases to form one kind of band, resulting in a decrease in the energy difference from the ground level. Accordingly, it is conceivable that the emission peak wavelength shifted to the long wavelength side as the increase in the Ce concentration.

In also Examples 5 to 10, each of the excitation spectra further had a peak in a wavelength range of 350 nm or more and less than 500 nm.

Evaluation of Internal Quantum Efficiency

Figure 19:
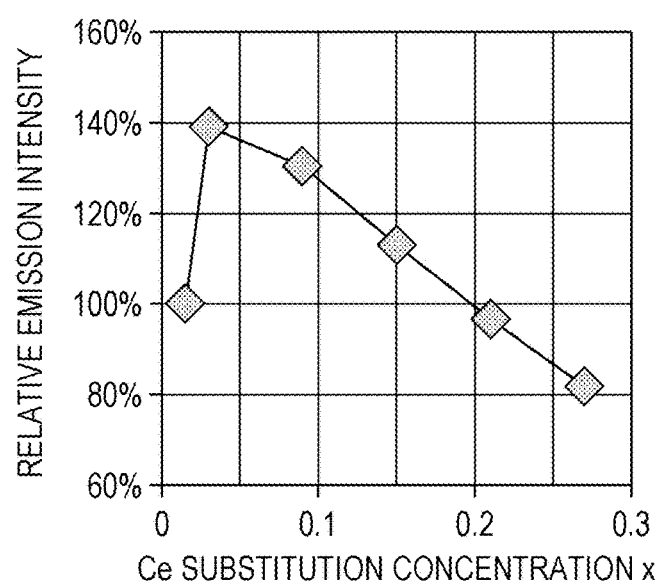
FIG. 19 is a graph showing a relationship between the Ce substitution concentrations and the relative emission intensities in Examples 5 to 10.

The quantum efficiency (IQE) in each of Examples 5 to 10 was measured with an absolute PL quantum yield spectrometer (C9920-02, manufactured by Hamamatsu Photonics K.K.). FIG. 19 shows the relative emission intensities in Examples 5 to 10. Herein, the relative emission intensity in this example refers to the relative value of each sample when IQE of Example 5 is defined as 100%.

FIG. 19 demonstrates that the relative emission intensity changes depending on the Ce concentration x in the phosphor. For example, in the range where the Ce substitution concentration x is higher than 0.03, the relative emission intensity decreases with an increase in the Ce substitution concentration x. This is probably caused by concentration quenching. In order to obtain light emission, it is necessary to contain Ce, and the value of x is therefore larger than 0. In addition, as shown in FIG. 19, the value of x is, for example, desirably 0.015 or more. The maximum value of x is not limited as long as the phosphor can emit light. However, when the value of x is too large, the emission intensity decreases due to concentration quenching. Accordingly, the value of x is desirably 0.6 or less. In addition, as shown in FIG. 19, the value of x is, for example, desirably 0.3 or less and more desirably 0.15 or less. For example, it was demonstrated that a phosphor having higher emission intensity can be realized by controlling the Ce substitution concentration x within the above range.

Evaluation of Emission Lifetime

The emission lifetimes in Examples 5 to 10 were measured with a fluorescence lifetime measuring apparatus (Quantaurus-Tau compact fluorescence lifetime spectrometer, manufactured by Hamamatsu Photonics K.K.). Table 7 shows 1/e emission lifetimes in Examples 5 to 10.

TABLE 7

|  | 1/e Emission lifetime |
| --- | --- |
| Example 5 | 64 ns |
| Example 6 | 60 ns |
| Example 7 | 56 ns |
| Example 8 | 49 ns |
| Example 9 | 45 ns |
| Example 10 | 42 ns |

In Examples 5 to 10, it was confirmed that the lie emission lifetimes were all 100 ns or less. Accordingly, the phosphors in Examples 5 to 10 can realize high-output light-emitting devices by being combined with high-output excitation light sources. An increase in Ce concentration allows energy transfer between neighboring Ce atoms to be readily caused, resulting in occurrence of migration of energy. During the occurrence of migration of energy, if an electron is captured by deficiency in a crystal, the migration is relieved as radiationless transition. That is, it is conceivable that the probability that electrons having a relatively low transition probability become nonradiative (radiationless transition) increases with an increase in the Ce concentration to decrease the emission lifetime.

Evaluation of Crystal Structure

The powder X-ray diffraction patterns in Examples 5 to 10 and Comparative Example 1 were measured with an X-ray diffraction measuring apparatus (RINT2100, manufactured by Rigaku Corporation). The measurement was performed using Cu-Kα radiation under conditions shown in Table 8.

TABLE 8

| Starting angle | Ending angle | Sampling width | Scanning speed | Tube voltage | Tube current | Diffusion slit | Scattering slit | Light-receiving slit |
|---|---|---|---|---|---|---|---|---|
| 10° | 60° | 0.01° | 1°/min | 40 kV | 40 mA | 1° | 1° | 0.15 mm |

Figure 20:
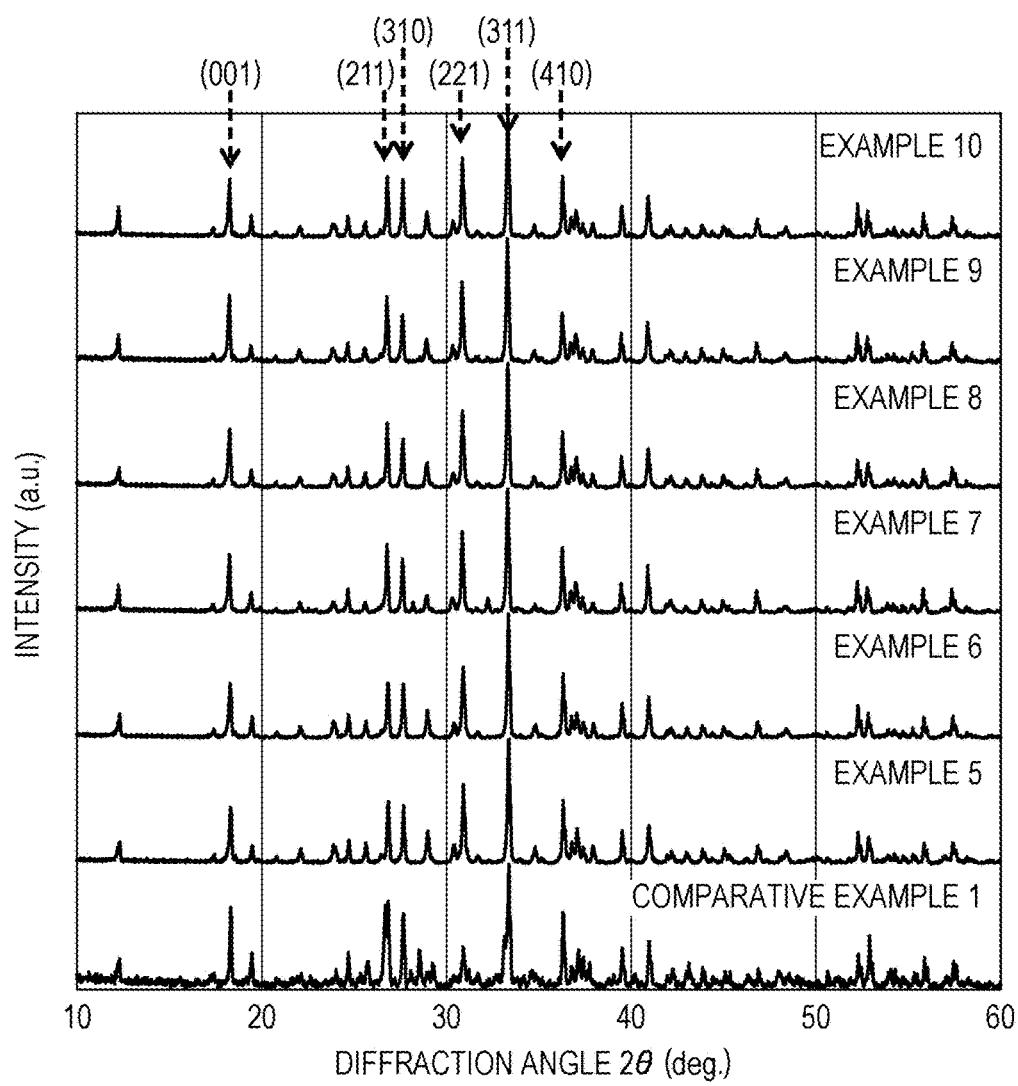
FIG. 20 shows XRD diffraction patterns of Examples 5 to 10 and Comparative Example 1.

The resulting X-ray diffraction patterns are shown in FIG. 20. FIG. 20 demonstrates that the X-ray diffraction patterns in Examples 5 to 10 slightly shifted to the low angle side with respect to the X-ray diffraction pattern obtained in Comparative Example 1, but both are almost the same.

In the resulting diffraction peaks, six diffraction peaks corresponding to the crystal form of $La_3Si_6N_{11}$ are defined as peaks 1 to 6 from the low angle side, and Table 9 shows the values of 2θ of the diffraction peaks.

TABLE 9

|  | Peak 1 | Peak 2 | Peak 3 | Peak 4 | Peak 5 | Peak 6 |
|---|---|---|---|---|---|---|
| Example 5 | 18.31° | 26.85° | 27.68° | 30.92° | 33.37° | 36.32° |
| Example 6 | 18.30° | 26.84° | 27.67° | 30.91° | 33.36° | 36.32° |
| Example 7 | 18.25° | 26.78° | 27.62° | 30.86° | 33.32° | 36.27° |
| Example 8 | 18.25° | 26.80° | 27.65° | 30.86° | 33.31° | 36.29° |
| Example 9 | 18.24° | 26.78° | 27.61° | 30.84° | 33.30° | 36.27° |
| Example 10 | 18.26° | 26.81° | 27.64° | 30.87° | 33.33° | 36.29° |

Table 9 demonstrates that the X-ray diffraction pattern of each of the resulting phosphors has diffraction peaks, corresponding to the peaks 1 to 6, in (1) 2θ: 17.8° or more and 18.8° or less, (2) 2θ: 26.2° or more and 27.2° or less, (3) 2θ: 27.2° or more and 28.2° or less, (4) 2θ: 30.5° or more and 31.5° or less, (5) 2θ: 32.8° or more and 33.8° or less, and (6) 2θ: 35.8° or more and 36.8° or less. The plane indices indicated by the peaks 1 to 6 were (001), (211), (310), (221), (311), and (410), respectively. These results suggest that the space group of each phosphor of Examples 5 to 10 is a tetragon as in Examples 1 to 4 and Comparative Example 1 and that the crystal structures are almost the same as that of the crystal represented by the formula $La_3Si_6N_{11}$.

Example 11 and Comparative Example 3

A method of producing a phosphor will now be shown. As starting materials, a LaN powder, a $Si_3N_4$ powder, an AlN powder, and a CeN powder were prepared. The LaN powder, the $Si_3N4$ powder, and the CeN powder were weighed so as to give a composition represented by the formula $La_{3-x}Ce_xSi_6N_{11}$ and were mixed. However, the LaN powder was weighed in an amount higher by 24% than the theoretical value. To this powder mixture, the AlN powder was added, followed by further mixing. The mixing was performed by dry blending using a mortar in a glove box under a nitrogen atmosphere. The mixed raw material powders were put in a boron nitride crucible. The raw material powders were fired in a 0.5 MPa nitrogen atmosphere at 1900° C. for 2 hours. The sample after the firing was washed in a 3% hydrochloric acid solution for 24 hours. The phosphors of Example 11 and Comparative Example 3 were produced from the starting materials shown in Table 10 according to the above method.

In Example 11, as in Examples 1 to 10, emission of red light having an emission peak wavelength of 600 nm or more was observed. An excitation peak wavelength of 500 nm or more was also observed.

TABLE 10

|  | LaN | $Si_3N_4$ | AlN | CeN | x | Emission peak wavelength | Excitation peak wavelength |
|---|---|---|---|---|---|---|---|
| Example 11 | 6.271 g | 3.305 g | 0.483 g | 0.490 g | 0.27 | 642 nm | 531 nm |
| Comparative Example 3 | 6.271 g | 3.305 g | 0 g | 0.490 g | 0.27 | 536 nm | 450 nm |

Evaluation of Emission Lifetime

The emission lifetimes in Example 11 and Comparative Example 3 were measured with a fluorescence lifetime measuring apparatus (Quantaurus-Tau compact fluorescence lifetime spectrometer, manufactured by Hamamatsu Photonics K.K.). Table 11 shows 1/e emission lifetimes in Example 11 and Comparative Example 3.

TABLE 11

|  | 1/e Emission lifetime |
|---|---|
| Example 11 | 49 ns |
| Comparative Example 3 | 38 ns |

In Example 11, it was confirmed that the 1/e emission lifetime was 100 ns or less.
Evaluation of Crystal Structure
The powder X-ray diffraction patterns of Example 11 and Comparative Example 3 were measured with an X-ray diffraction measuring apparatus (RINT2100, manufactured by Rigaku Corporation). The measurement was performed using Cu-Kα radiation under conditions shown in Table 8. The resulting X-ray diffraction patterns are shown in FIGS. 21A and 21B.

It was demonstrated that the X-ray diffraction pattern of Example 11 was almost the same as that of Comparative Example 3. It was also demonstrate that the X-ray diffraction peaks in Example 11 slightly shifted to the low angle side with respect to the X-ray diffraction peaks in Comparative Example 3.

In the resulting diffraction peaks, six diffraction peaks corresponding to the crystal form of $La_3Si_6N_{11}$ are defined as peaks 1 to 6 from the low angle side, and Table 12 shows the values of 2θ of the diffraction peaks.

TABLE 12

| | Peak 1 | Peak 2 | Peak 3 | Peak 4 | Peak 5 | Peak 6 |
|---|---|---|---|---|---|---|
| Example 11 | 18.23° | 26.75° | 27.60° | 30.82° | 33.28° | 36.25° |
| Comparative Example 3 | 18.30° | 26.84° | 27.66° | 30.91° | 33.37° | 36.32° |

Table 12 demonstrates that the X-ray diffraction pattern of each of the resulting phosphors has diffraction peaks, corresponding to the peaks 1 to 6, in (1) 2θ: 17.8° or more and 18.8° or less, (2) 2θ: 26.2° or more and 27.2° or less, (3) 2θ: 27.2° or more and 28.2° or less, (4) 2θ: 30.5° or more and 31.5° or less, (5) 2θ: 32.8° or more and 33.8° or less, and (6) 2θ: 35.8° or more and 36.8° or less. The plane indices indicated by the peaks 1 to 6 were (001), (211), (310), (221), (311), and (410), respectively. These results suggest that the space group of phosphor of Example 11 is a tetragon as in Examples 1 to 10 and Comparative Examples 1 and 3 and that the crystal structure is almost the same as that of the crystal represented by the formula $La_3Si_6N_{11}$.

Evaluation of Composition

The composition analysis of Example 11 and Comparative Example 3 was performed by inductively coupled plasma-atomic emission spectroscopy (ICP-AES). The pretreatment for the measurement will now be shown. Alkali fusion was performed using sodium peroxide, and the melt was dissolved in hydrochloric acid. The solution was diluted with pure water, and the content of Si was analyzed. In addition, alkali fusion was performed using lithium tetraborate and sodium carbonate, and the melt was dissolved in hydrochloric acid. The solution was diluted with pure water, and the contents of La, Al, and Ce were analyzed. The results are shown in Table 13.

TABLE 13

| | La | Ce | Al | Si |
|---|---|---|---|---|
| Example 11 | 4.85 mass % | 4.00 mass % | 4.89 mass % | 20.5 mass % |
| Comparative Example 3 | 50.6 mass % | 4.26 mass % | 0 mass % | 23.1 mass % |

Table 13 demonstrates that Al was contained in Example 11.

Table 14 shows molar ratio of each element when the total content of Al and Si is converted to 6 mol.

TABLE 14

| | La | Ce | Al | Si |
|---|---|---|---|---|
| Example 11 | 2.30 mol | 0.19 mol | 1.19 mol | 4.81 mol |
| Comparative Example 3 | 2.66 mol | 0.22 mol | 0 mol | 6 mol |

Table 14 demonstrates that the total content of La and Ca in each of the samples of Example 11 and Comparative Example 3 is lower than the stoichiometric composition (3 mol). This is probably caused by decomposition of LaN and CeN as the starting materials during firing. Thus, the amounts of La and Ce may be smaller than the stoichiometric composition as long as light emission is possible. For example, the total content of La and Ce may be 2 mol or more and 3 mol or less.

The contents of nitrogen and oxygen were then analyzed. The samples of Example 11 and Comparative Example 3 were melted in an inert gas at 2300° C. The oxygen amount was measured by nondispersive infrared absorption spectroscopy (NDIR), and the nitrogen amount was measured by thermal conductivity detection (TCD). The results are shown in Table 15.

TABLE 15

| | O | N |
|---|---|---|
| Example 11 | 0.5 mass % | 21.4 mass % |
| Comparative Example 3 | 1.4 mass % | 20.6 mass % |

Table 15 demonstrates that the sample of Example 11 contained O. Thus, O may be contained as long as light emission is possible. It is difficult to simultaneously quantify the absolute amounts of an anion and a cation, the absolute value of the content of each element shown in Tables 13 to 15 includes an error. Accordingly, the composition of a phosphor of the present disclosure is not interpreted limitedly by the absolute value of each element shown in Tables 13 to 15.

Evaluation of Local Structure of Ce Ligand

The local structures of Ce ligands in Example 11 and Comparative Example 3 were measured by X-ray absorption fine structure spectroscopy (XAFS). The XAFS measurement may use Beamline 16B2 of Spring 8, RIKEN, Institute of Physical and Chemical Research.

The pretreatment for the measurement will now be shown. The sample (0.16 g) of Example 11 and a BN power (0.01 g) were mixed in a mortar, and a pellet having a diameter of 8 mm was produced by metallic molding. Similarly, the sample (0.16 g) of Comparative Example 3 and a BN powder (0.01 g) were mixed in a mortar, and a pallet having a diameter of 8 mm was produced by metallic molding. In order to reveal the local structures of Ce and ligands in the vicinity thereof, the absorption spectrum near the K-absorption edge of Ce was measured. Extended X-ray absorption fine structure (EXAFS) vibration was analyzed with EXAFS analysis software, Athena, which is an open source to obtain the radial distribution function in the vicinity of the Ce atom.

The parameters used in the analysis are shown in Table 16.

TABLE 16

| Background removal parameters | |
|---|---|
| E0 | 40463.755 |
| Algorithm | autobk |
| Rbkg | 1.000 |
| k-weight | 2 |
| Normalization order | 3 |
| Pre-edge range | [−150.000:−75.000] |
| Normalization range | [150.000:1400.778] |
| Spline range (k) | [0.000:12.000] |
| Spline range (E) | [0.000:548.638] |
| Edge step | 3.64E-01 |
| Standard | None |
| Lower clamp | None |
| Upper clamp | Strong |
| Forward Fourier transform parameters | |

TABLE 16-continued

| | |
|---|---|
| k-range | [3.000:17.847] |
| dk | 1.000 |
| Window | hanning |
| Arb. kw | 0.5 |
| Phase correction | no |
| Backward Fourier transform parameters | |
| R-range | [1.000:3.000] |
| dR | 0.000 |
| Window | hanning |
| Plotting parameters | |
| Plot multiplier | 1.00E+00 |
| y offset | 0.000 |

Figure 22:
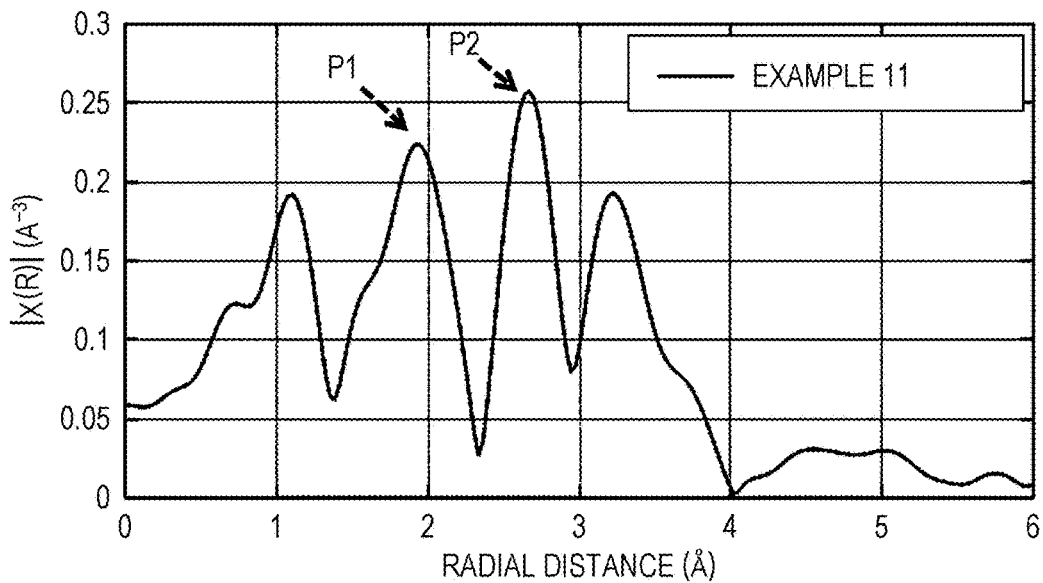
FIG. 22 is a graph showing the radial distribution function in the vicinity of a Ce atom in Example 11.
Figure 23:
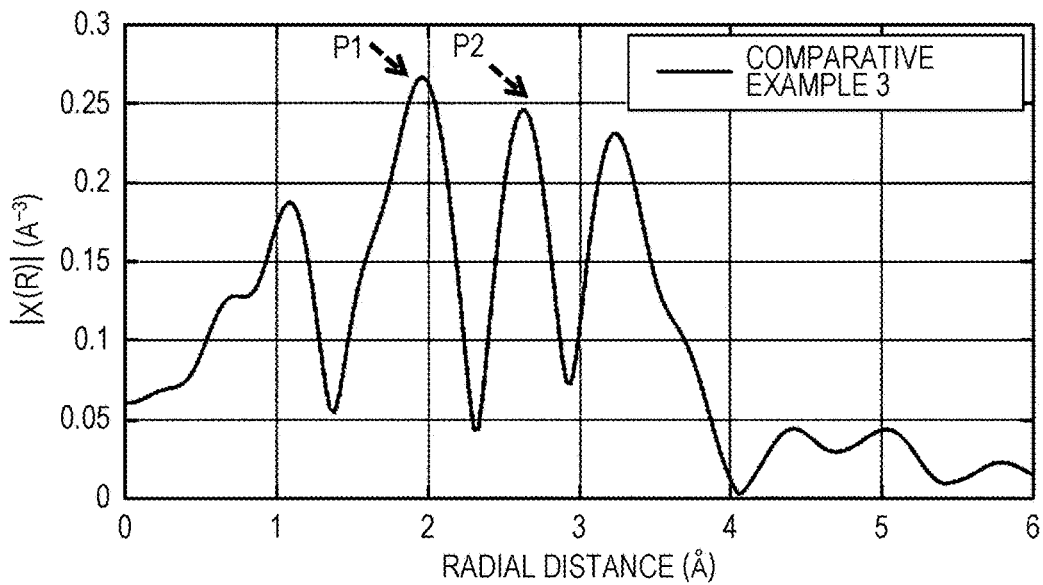
FIG. 23 is a graph showing the radial distribution function in the vicinity of a Ce atom in Comparative Example 3.

FIG. 22 is a graph showing the radial distribution function of Example 11. FIG. 23 is a graph showing the radial distribution function of Comparative Example 3. In general, the horizontal axis (radial distance) of a radial distribution function corresponds to the distance to the adjacent atom. The vertical axis (peak height) shows the coordination number n. In FIGS. 22 and 23, the peak at about 1.1 angstroms is a ghost peak due to noise of measured signals. The peak (P1) at about 1.9 angstroms is a peak of the first neighbor shell of Ce. The peak (P2) at about 2.6 angstroms is a peak of the second neighbor shell of Ce. The peak at about 3.3 angstroms is a peak of the third neighbor shell of Ce.

As obvious from FIG. 23, in Comparative Example 3, the height of the peak (P1) of the first neighbor shell is higher than that of the peak (P2) of the second neighbor shell. In addition, as obvious from FIG. 22, in Example 11, the height of the peak (P1) of the first neighbor shell is lower than (about 0.84 times) that of the peak (P2) of the second neighbor shell The height of P2 of Example 11 is almost equal to that of P2 of Comparative Example 3, whereas the height of P1 of Example 11 is obviously lower than that of P1 of Comparative Example 3.

The above results demonstrate that the coordination number of the first neighbor shell of Ce in Example 11 is smaller than that of the first neighbor shell of Ce in Comparative Example 3.

The radial distribution functions of FIGS. 22 and 23 were analyzed for coordinating atoms with EXAFS analysis software, Artemis, which is an open source. The results revealed that the Ce atom is substituted for the A-site of La of the crystal structure in both Example 11 and Comparative Example 3. It was revealed that in Example 11, seven nitrogen atoms are coordinated to the first neighbor shell of Ce, whereas in Comparative Example 3, eight nitrogen atoms are coordinated to the first neighbor shell of Ce.

The above results revealed that the coordination structure in the vicinity of Ce in Comparative Example 3 is a structure in which eight nitrogen atoms are coordinated as in the A-site of La in $La_3Si_6N_{11}$ and is a structure having relatively high symmetry, It was also revealed that the coordination structure in the vicinity of Ce in Example 11 is a structure having nitrogen deficiency introduced in the vicinity of the A-site of La in $La_3Si_6N_{11}$ and is a coordination structure of heptacoordination showing low symmetry.

Thus, it is conceivable that in Example 11, since the symmetry of the coordination structure in the vicinity of Ce decreases due to, for example, a frenkel defect, the splitting of the 5$d$ orbit is enhanced to decrease the energy difference from the 4$f$ orbit. Accordingly, it is conceivable that the emission wavelength is increased to realize a Ce based phosphor emitting red light.

Although the phosphors of Examples 1 to 11 each have almost the same crystal structure as that of the crystal represented by the formula $La_3Si_6N_{11}$, the phosphors emit red light on the longer wavelength side compared to known LSN:Ce yellow phosphors. Although the reason of this is not necessarily obvious, for example, the following possibilities are conceivable: The phosphors of Examples 1 to 11 differ from known phosphors in that Al (e.g., AlN powder) is contained in the raw materials, and thereby emission of red light is realized. In addition, the phosphors of Examples 1 to 11, for example, each have a crystal structure substituted by Ce for a part of the A-site of La, substituted by Al for a part of Si (or substituted by Al-O for a part of Si-N) in the vicinity of Ce, and having a deficit of a part of N in an $La_3Si_6N_{11}$ crystal, and thereby emission of red light is realized.

The phosphor of the present disclosure is useful as, for example, a light-emitting apparatus. The phosphor can be used as a light source of, for example, a general lighting system, such as a ceiling light; a special lighting system, such as a spotlight, stadium lighting, and studio lighting; a vehicle lighting system, such as a head lamp; a projection apparatus, such as a projector and a head-up display; an image pickup apparatus, such as an endoscopic light, a digital camera, a mobile phone, and a smartphone; and a liquid crystal display, such as a monitor for a personal computer (PC), notebook personal computer, television, portable digital assistant (PDX), smartphone, tablet PC, or mobile phone.

What is claimed is:

1. A phosphor comprising a crystal phase having a chemical composition $Ce_xM_{3-x-y}\beta_6\gamma_{11-z}$, where M is one or more elements selected from the group consisting of Sc, Y, La, Pr, Nd, Sm, Eu, Gd, Tb, Dy, Ho, Er, Tm, Yb, and Lu;

β contains Si in an amount of 50 mol % or more of a total mol of β;

γ contains N in an amount of 80 mol % or more of a total mol of γ;

0<x≤0.6;

0≤y≤1.0; and

0≤z≤1.0, wherein the phosphor shows:

a maximum peak of an emission spectrum in a wavelength range of 600 nm or more and 800 nm or less; and a first peak of an excitation spectrum in a wavelength range of 500 nm or more and 600 nm or less.

2. The phosphor according to claim 1, wherein the M contains La in an amount of 90 mol % or more of a total mol of M.

3. The phosphor according to claim 1, wherein the β further contains one or two elements selected from the group consisting of Al and Ga.

4. The phosphor according to claim 3, wherein the β contains the one or two elements in an amount (100×/6) mol % or more of the total mol of β.

5. The phosphor according to claim 1, wherein the y further contains O.

6. The phosphor according to claim 1, wherein the x satisfies 0.015≤x≤0.3.

7. The phosphor according to claim 1, wherein the phosphor shows a second peak of the excitation spectrum in a wavelength range of 350 nm or more and less than 500 nm.

8. The phosphor according to claim 7, wherein the first or second peak is the maximum peak of the excitation spectrum.

9. The phosphor according to claim 1, wherein
the crystal phase has a 1/e emission lifetime of 100 ns or less.

10. The phosphor according to claim 1, wherein the crystal phase shows diffraction peaks in
(1) 2θ: 17.8° or more and 18.8° or less;
(2) 2θ: 26.2° or more and 27.2° or less;
(3) 2θ: 27.2° or more and 28.2° or less;
(4) 2θ: 30.5° or more and 31.5° or less
(5) 2θ: 32.8° or more and 33.8° or less; and
(6) 2θ: 35.8° or more and 36.8° or less
in an X-ray diffraction pattern measured with Cu-Kα radiation.

11. The phosphor according to claim 1, wherein
in an EXAFS radial distribution function spectrum at K-absorption edge of Ce, a first neighbor shell of Ce has a peak having a height lower than that of a peak of a second neighbor shell of Ce.

12. A phosphor comprising a crystal phase having a chemical composition $Ce_xM_{3-x-y}\beta_6\gamma_{11-z}$, where
M is one or more elements selected from the group consisting of Sc, Y, La, Pr, Nd, Sm, Eu, Gd, Tb, Dy, Ho, Er, Tm, Yb, and Lu;
β contains Si in an amount of 50 mol % or more of a total mol of β;
γ contains N in an amount of 80 mol % or more of a total mol of γ;
$0<x\leq 0.6$;
$0\leq y\leq 1.0$; and
$0\leq z\leq 1.0$, wherein
in an EXAFS radial distribution function spectrum at K-absorption edge of Ce, a first neighbor shell of Ce has a peak having a height lower than that of a peak of a second neighbor shell of Ce.

13. The phosphor according to claim 11, wherein
the height of the peak of the first neighbor shell is 0.8 times or more and 0.9 times or less the height of the peak of the second neighbor shell.

14. The phosphor according to claim 1, wherein
in an EXAFS radial distribution function spectrum at K-absorption edge of Ce, the coordination number of a first neighbor shell of Ce is seven.

15. A phosphor comprising:
a crystal phase having a chemical composition $Ce_xM_{3-x-y}\beta_6\gamma_{11-z}$, where
M is one or more elements selected from the group consisting of Sc, Y, La, Pr, Nd, Sm, Eu, Gd, Tb, Dy, Ho, Er, Tm, Yb, and Lu;
β contains Si in an amount of 50 mol % or more of a total mol of β;
γ contains N in an amount of 80 mol % or more of a total mol of γ;
$0<x\leq 0.6$;
$0\leq y\leq 1.0$; and
$0\leq z\leq 1.0$, wherein
in an EXAFS radial distribution function spectrum at K-absorption edge of Ce, the coordination number of a first neighbor shell of Ce is seven.

16. The phosphor according to claim 1, wherein
the y is 0 and the z is 0.

17. A light-emitting apparatus comprising:
an excitation light source emitting light of a wavelength of 600 nm or less; and
a phosphor that is irradiated with the light emitted by the excitation light source and emits fluorescence having a wavelength longer than a wavelength of the light emitted by the excitation light source, wherein
the phosphor comprises a crystal phase having a chemical composition $Ce_xM_{3-x-y}\beta_6\gamma_{11-z}$, where
M is one or more elements selected from the group consisting of Sc, Y, La, Pr, Nd, Sm, Eu, Gd, Tb, Dy, Ho, Er, Tm, Yb, and Lu;
β contains Si in an amount of 50 mol % or more of a total mol of β;
γ contains N in an amount of 80 mol % or more of a total mol of γ;
$0<x\leq 0.6$;
$0\leq y\leq 1.0$; and
$0\leq z\leq 1.0$, and
the phosphor shows:
a maximum peak of an emission spectrum in a wavelength range of 600 nm or more and 800 nm or less; and
a first peak of an excitation spectrum in a wavelength range of 500 nm or more and 600 nm or less.

18. The light-emitting apparatus according to claim 17, wherein
the excitation light source emits the light having a wavelength of 500 nm or more and 600 nm or less.

19. The light-emitting apparatus according to claim 17, wherein
the excitation light source emits the light having a wavelength of 420 nm or more and 480 nm or less.

20. The light-emitting apparatus according to claim 17, wherein
the excitation light source is an LED or an LD.

21. The light-emitting apparatus according to claim 17, wherein
the phosphor is a first phosphor,
the light-emitting apparatus further comprises a second phosphor that is irradiated with the light emitted by the excitation light source and emits fluorescence having a wavelength longer than a wavelength of the light emitted by the excitation light source, and
the second phosphor shows a maximum peak of an emission spectrum in a wavelength range of 500 nm or more and 600 nm or less.

22. The light-emitting apparatus according to claim 21, wherein
the second phosphor emits yellow light, and
the light-emitting apparatus further comprises a third phosphor that is irradiated with the light emitted by the excitation light source and emits green light.

* * * * *